(12) United States Patent
Confalone et al.

(10) Patent No.: US 6,175,009 B1
(45) Date of Patent: Jan. 16, 2001

(54) PROCESS FOR THE PREPARATION OF QUINAZOLINONES

(75) Inventors: Pasquale Nicholas Confalone, Greenville; Nicholas Andrew Magnus, Wilmington; Louis Storace, Middletown, all of DE (US)

(73) Assignee: Dupont Pharmaceuticals Company, Wilmington, DE (US)

( * ) Notice: Under 35 U.S.C. 154(b), the term of this patent shall be extended for 0 days.

(21) Appl. No.: 09/442,598

(22) Filed: Nov. 18, 1999

Related U.S. Application Data

(60) Provisional application No. 60/109,251, filed on Nov. 19, 1998.

(51) Int. Cl.[7] .................................................. C07D 239/80
(52) U.S. Cl. ........................................... 544/285; 544/286
(58) Field of Search ....................................... 544/286, 285

(56) References Cited

FOREIGN PATENT DOCUMENTS

| 0530994 | 3/1993 | (EP) . |
|---|---|---|
| 9845276 | 10/1988 | (WO) . |
| 9304047 | 3/1993 | (WO) . |
| 93/04047 | * 3/1993 | (WO) . |

OTHER PUBLICATIONS

Sternbach et al, *J. Org Chem.* 1966, 31, 1007–1009, "Quinazolines and 1, 4–Benzodiazepines. XXVIII. Substitued 2 (3H) –Quinazolines and Quinazolinethiones."

* cited by examiner

*Primary Examiner*—Mukund J. Shah
*Assistant Examiner*—Hong Liu

(57) ABSTRACT

The present invention relates generally to an asymmetric synthesis of 4,4-disubstituted-3,4-dihydro-2(1H)-quinazolinones, and intermediates thereof. The target compounds are useful for the treatment of human immunodeficiency virus (HIV) as an inhibitor of reverse transcriptase.

25 Claims, No Drawings

PROCESS FOR THE PREPARATION OF QUINAZOLINONES

This application claims the benefit of U.S. Provisional Application No. 60/109,251, filed Nov. 19, 1998.

FIELD OF THE INVENTION

The present invention relates generally to an asymmetric synthesis of 4,4-disubstituted-3,4-dihydro-2(1H)-quinazolinones, and intermediates thereof. The target compounds are useful for the treatment of human immunodeficiency virus (HIV) as an inhibitor of reverse transcriptase.

BACKGROUND

Reverse transcription is a common feature of retrovirus replication. Viral replication requires a virally encoded reverse transcriptase to generate DNA copies of viral sequences by reverse transcription of the viral RNA genome. Reverse transcriptase, therefore, is a clinically relevant target for the chemotherapy of retroviral infections because the inhibition of virally encoded reverse transcriptase would interrupt viral replication.

An extremely promising and active area of research is in the discovery of non-nucleoside HIV reverse transcriptase inhibitors. Commonly assigned U.S. patent application Ser. No. 09/056,820(PCT Application WO98/45276) discloses novel quinazolinones of formula (I) as active non-nucleoside HIV reverse transcriptase inhibitors.

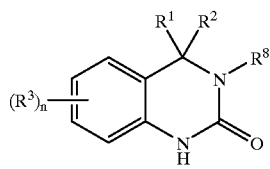

(I)

Due to the importance of this structural class, methods to synthesize the quinazolinone core which are amenable to industrial manufacture are needed.

Previous methods to prepare quinazolinones have employed dehydration of a quinazolinone, followed by 1,4 nucleophilic addition. Sternbach et al., Journal of Organic Chemistry, 1966, 31, 1007. International publication WO 93/04047 discloses the application of this methodology to the preparation of quinazolinone derivatives which are inhibitors of HIV reverse transcriptase (Scheme 1).

Scheme 1

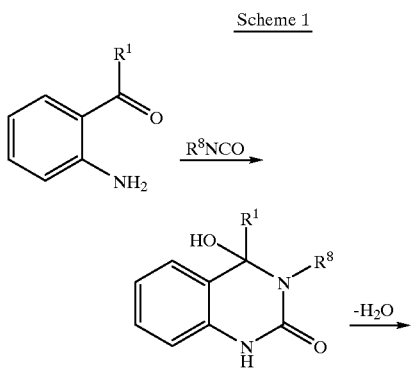

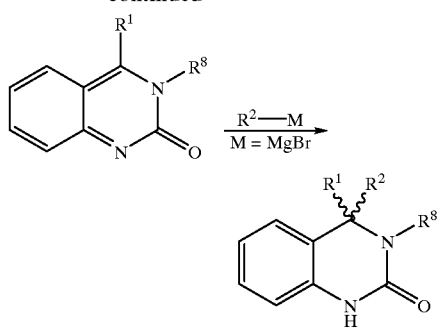

In this methodology, however, the 1,4 addition of $R^2$ occurs without stereoselectivity. A manufacturing process which attempts to exploit this teaching would require tedious separation of the undesired enantiomer, making this approach unfeasible for reasons related to both cost and scale. Moreover, the dehydration protocol teaches thermal conditions, which may prove hazardous on an industrial scale.

The present invention finds utility in the asymmetric preparation of quinazolinone derivatives. By dehydrating a quinazolinone containing a chiral $R^8$, the subsequent 1,4 nucleophilic addition is directed to afford the desired stereochemistry (Scheme 2). Removal of the directing group then affords the target compound.

Scheme 2

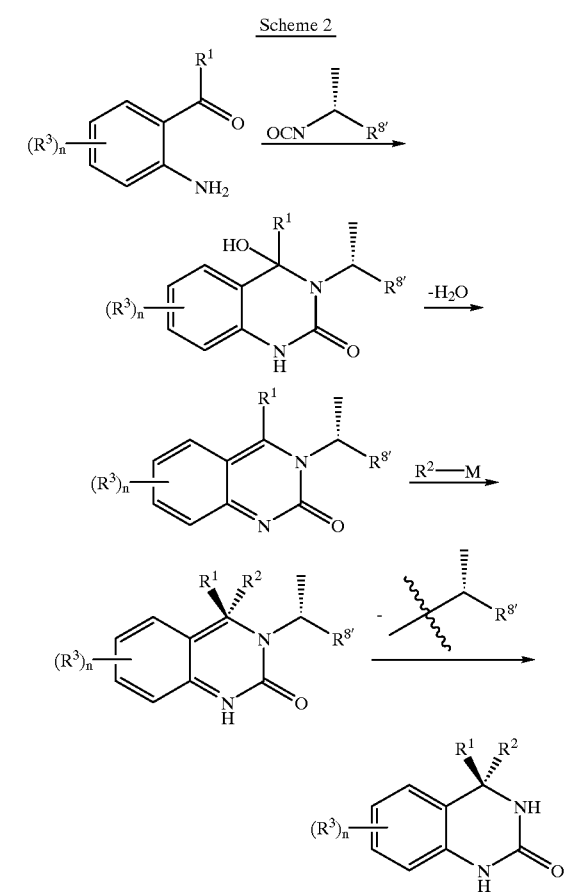

The dehydration of the hemiaminal preferably occurs through the use of a dehydrating agent. This discovery allows for the safe preparation of electron deficient quinazolinones which are known to be resistant to dehydration. Additionally, convenient conditions for the preparation of the desired hemiaminal from an α-ketoaniline and a chiral isocyanate are disclosed. As a result, these important compounds can be prepared safely and efficiently.

SUMMARY OF THE INVENTION

The present invention relates generally to processes for the efficient production of 4,4-disubstituted-3,4-dihydro-2 (1H)-quinazolinones (I):

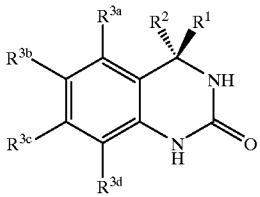
(I)

and intermediates thereof;
wherein $R^1$, $R^2$, $R^{3a}$, $R^{3b}$, $R^{3c}$, and $R^{3d}$ are defined below, which has been achieved by the inventors' discovery that a compound of formula (I) or a pharmaceutically acceptable salt form thereof, is formed by a high yielding and chiral process, comprising:

step (1), contacting a compound of formula (II):

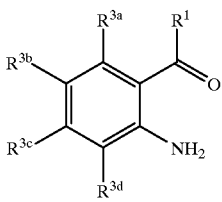
(II)

or a salt form or a hydrate of the salt form thereof; with an isocyanate of formula (III):

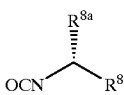
(III)

wherein $R^8$ and $R^{8a}$ are defined below;
to form a compound of formula (II-a):

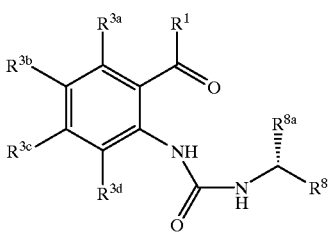
(II-a)

or a salt form thereof;
step (1-i), cyclizing the compound of formula (II-a) to form a compound of formula (IV):

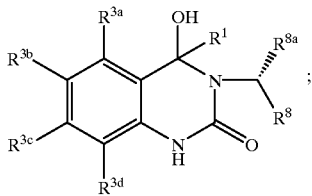
(IV)

step (2), dehydrating the compound of formula (IV) to form a compound of formula (V):

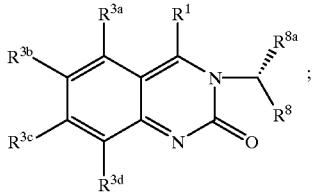
(V)

step (2-i), contacting the compound of formula (V) with a nucleophile of formula (VI):

(VI)

$R^2$—M wherein M is a metal counterion;
to form a compound of formula (VII):

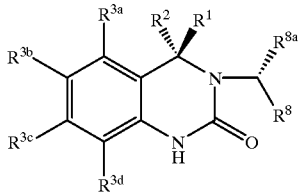
(VII)

or a salt form thereof; and
step (3), ionizing the compound of formula (VII) to form a compound of formula (I), or a pharmaceutically acceptable salt form thereof.

DETAILED DESCRIPTION OF THE INVENTION

[1] Thus, in a first embodiment, the present invention describes a novel process for the preparation of a compound of formula (I):

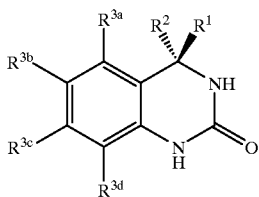

wherein:
- $R^1$ is $C_{1-3}$ alkyl substituted with 1–7 halogen;
- $R^2$ is selected from $C_{1-5}$ alkyl substituted with 1–2 $R^4$, $C_{2-5}$ alkenyl substituted with 1–2 $R^4$, $C_{2-5}$ alkynyl substituted with 1 $R^4$, and $OR^{2a}$;
- $R^{2a}$ is $C_{1-4}$ alkyl;
- $R^{3a}$ is H;
- $R^{3b}$ is selected from H, $C_{1-4}$ alkyl, $C_{1-4}$ alkoxy, F, Cl, Br, I, and $NR^5R^{5a}$;
- $R^{3c}$ is selected from H, $C_{1-4}$ alkyl, $C_{1-4}$ alkoxy, F, Cl, Br, I, and $NR^5R^{5a}$;
- $R^{3d}$ is selected from H, $C_{1-4}$ alkyl, $C_{1-4}$ alkoxy, F, Cl, Br, I, and $NR^5R^{5a}$;
- alternatively, $R^{3a}$ and $R^{3b}$ combine to form —$OCH_2O$—;
- $R^4$ is selected from $C_{3-5}$ cycloalkyl substituted with 0–2 $R^{4a}$, phenyl substituted with 0–5 $R^{4a}$, and a 5–6 membered heterocyclic system containing 1–3 heteroatoms selected from O, N, and S, substituted with 0–2 $R^{4a}$;
- $R^{4a}$ is selected from $C_{1-3}$ alkyl, Cl, Br, F, I, $OCH_3$, $SCH_3$, and $NR^5R^{5a}$; and
- $R^5$ and $R^{5a}$ are independently selected from H and $C_{1-3}$ alkyl;

the process comprising:

step (1), contacting a compound of formula (II):

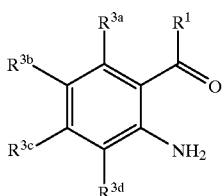

or a salt form or a hydrate of the salt form thereof;
with an isocyanate of formula (III):

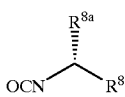

wherein:
- $R^{8a}$ is selected from methyl, ethyl, propyl, and isopropyl;
- $R^8$ is selected from phenyl substituted with 0–3 $R^9$, and naphthyl substituted with 0–3 $R^9$; and
- $R^9$ is selected from $C_{1-4}$ alkyl, $C_{1-4}$ alkoxy, F, Cl, Br, and I;

to form a compound of formula (II-a):

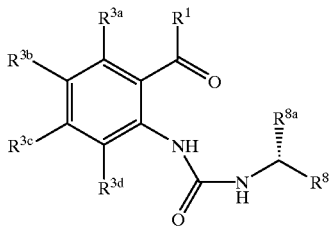

or a salt form thereof;

step (1-i), cyclizing the compound of formula (II-a) to form a compound of formula (IV):

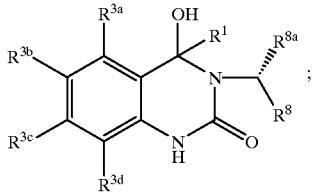

step (2), dehydrating the compound of formula (IV) to form a compound of formula (V):

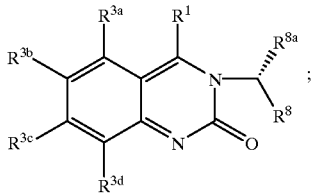

step (2-i), contacting the compound of formula (V) with a nucleophile of formula (VI):

$R^2$—M wherein M is a metal counterion;
to form a compound of formula (VII):

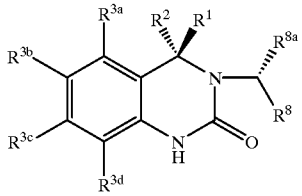

or a salt form thereof; and
step (3), ionizing the compound of formula (VII) to form a compound of formula (I), or a pharmaceutically acceptable salt form thereof.

[2] In a preferred embodiment, $R^1$ is $CF_3$;

$R^2$ is selected from ethene substituted with cyclopropyl and ethyne substituted with cyclopropyl;

$R^{3a}$ is H;

$R^{3b}$ is Cl;

$R^{3c}$ and $R^{3d}$ are H;

$R^{8a}$ is $CH_3$;

$R^8$ is phenyl;

M is a counter ion selected from $Li^+$, $Na^+$, $K^+$, $CuCl^+$, $CuBr^+$, $MgCl^+$, $MgI^+$, and $MgBr^+$; and wherein:

step (1) comprises contacting the compound of formula (II) with the isocyanate of formula (III) in the presence of a first strong acid;

step (1-i) comprises cyclizing the compound of formula (II-a) by heating the compound of formula (II-a) to a temperature in the range of about 50° C. to about 70° C.;

step (2) comprises dehydrating the compound of formula (IV) by contacting the compound of formula (IV) with at least one equivalent of a dehydrating agent in the presence of suitable amount of a base;

step (2-i) comprises contacting the compound of formula (V) with the nucleophile of formula (VI) by adding the nucleophile of formula (VI) to the compound of formula (V) at a suitable temperature to form the compound of formula (VII); and step (3) comprises ionizing the compound of formula (VII) by contacting the compound of formula (VII) with a second strong acid to form a compound of formula (I) or a pharmaceutically acceptable salt form thereof.

[3] In a more preferred embodiment, the first strong acid is selected from trifluoroacetic acid, formic acid, methanesulfonic acid, nitric acid, sulfuric acid, hydrochloric acid; trimethylsilyl chloride, trimethylsilyl iodide, trimethylsilyl bromide, trimethyl silyl cyanide, triisopropylsilyl chloride, t-butyldimethylsilyl chloride, t-butyldiphenylsilyl chloride, triethylsilyl chloride, and trimethylsilyl trifluoromethanesulfonate;

the dehydrating agent is selected from methanesulfonyl chloride, thionyl chloride, acetyl chloride, and triphenylphosphine;

the amount of base in step (2) is in the range of about 2 to about 7 molar equivalents and the base is selected from triethylamine, N-methylmorpholine, N,N-diisopropylethylamine, pyridine, 1,4-diazabicyclo[2.2.2]octane, 1,8-diazabicyclo[5.4.0]undec-7-ene, tetramethylethylenediamine, and N,N-dimethylaminopyridine;

the suitable temperature to form the compound of formula (VII) is less than 0° C.; and the second strong acid is selected from trifluoroacetic acid, formic acid, and methanesulfonic acid.

[4] In an even more preferred embodiment, the first strong acid is hydrochloric acid, the dehydrating agent is thionyl chloride, the base is triethylamine, and the second strong acid is formic acid.

[5] In another even more preferred embodiment, the first strong acid is trimethylsilyl chloride.

[6] In another even more preferred embodiment, the base is N-methylmorpholine.

[7] In another even more preferred embodiment, the first strong acid is trimethylsilyl chloride, the dehydrating agent is thionyl chloride, the base is N-methylmorpholine, and the second strong acid is formic acid.

[8] In a second embodiment, the present invention describes a novel process for the preparation of a compound of formula (VII):

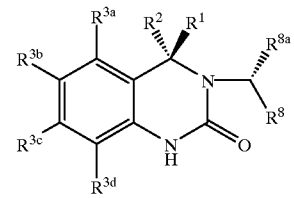

(VII)

or a salt form thereof; wherein:

$R^1$ is $C_{1-3}$ alkyl substituted with 1–7 halogen;

$R^2$ is selected from $C_{1-5}$ alkyl substituted with 1–2 $R^4$, $C_{2-5}$ alkenyl substituted with 1–2 $R^4$, $C_{2-5}$ alkynyl substituted with 1 $R^4$, and $OR^{2a}$;

$R^{2a}$ is selected from $C_{1-4}$ alkyl;

$R^{3a}$ is H;

$R^{3b}$ is selected from H, $C_{1-4}$ alkyl, $C_{1-4}$ alkoxy, F, Cl, Br, I, and $NR^5R^{5a}$;

$R^{3c}$ is selected from H, $C_{1-4}$ alkyl, $C_{1-4}$ alkoxy, F, Cl, Br, I, and $NR^5R^{5a}$;

$R^{3d}$ is selected from H, $C_{1-4}$ alkyl, $C_{1-4}$ alkoxy, F, Cl, Br, I, and $NR^5R^{5a}$;

alternatively, $R^{3a}$ and $R^{3b}$ combine to form —$OCH_2O$—;

$R^4$ is selected from $C_{3-5}$ cycloalkyl substituted with 0–2 $R^{4a}$, phenyl substituted with 0–5 $R^{4a}$, and a 5–6 membered heterocyclic system containing 1–3 heteroatoms selected from O, N, and S, substituted with 0–2 $R^{4a}$;

$R^{4a}$ is selected from $C_{1-3}$ alkyl, Cl, Br, F, I, $OCH_3$, $SCH_3$, and $NR^5R^{5a}$;

$R^5$ and $R^{5a}$ are independently selected from H and $C_{1-3}$ alkyl;

$R^{8a}$ is selected from methyl, ethyl, propyl, and isopropyl;

$R^8$ is selected from phenyl substituted with 0–3 $R^9$, and naphthyl substituted with 0–3 $R^9$; and $R^9$ is selected from $C_{1-4}$ alkyl, $C_{1-4}$ alkoxy, F, Cl, Br, and I;

the process comprising:

step (2), dehydrating a compound of formula (IV)

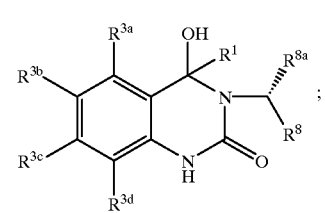

(IV)

to form a compound of formula (V):

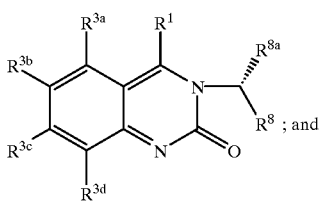

step (2-i), contacting the compound of formula (V) with a nucleophile of formula (VI):

$$R^2—M \quad (VI)$$

wherein M is a metal counterion;
to form a compound of formula (VII).

[9] In a preferred embodiment, $R^1$ is $CF_3$;
$R^2$ is selected from ethene substituted with cyclopropyl and ethyne substituted with cyclopropyl;
$R^{3a}$ is H;
$R^{3b}$ is Cl;
$R^{3c}$ and $R^{3d}$ are H;
$R^{8a}$ is $CH_3$;
$R^8$ is phenyl; and
M is a counter ion selected from $Li^+$, $Na^+$, $K^+$, $CuCl^+$, $CuBr^+$, $MgCl^+$, $MgI^+$, and $MgBr^+$.

[10] In another preferred embodiment, the process is carried out in a suitable solvent, and further comprising crystallizing the compound of formula (VII) by contacting the suitable solvent with a crystallization solvent.

[11] In another preferred embodiment, step (2) comprises dehydrating the compound of formula (IV) by contacting the compound of formula (IV) with at least one equivalent of a dehydrating agent in the presence of a suitable amount of base to form a compound of formula (V); and step (2-i) comprises contacting the compound of formula (V) with the nucleophile of formula (VI) by adding the nucleophile of formula (VI) to the compound of formula (V) at a suitable temperature to form the compound of formula (VII).

[12] In a more preferred embodiment, step (2) further comprises:
a) contacting the compound of formula (IV) with at least one equivalent of a dehydrating agent in the presence of a base to form a compound of formula (V) and a precipitated amine salt of the base; and
b) separating the precipitated amine salt of the base from the compound of formula (V).

[13] In an even more preferred embodiment, step (2) further comprises:
a) contacting the compound of formula (IV) with at least one equivalent of a dehydrating agent in the presence of a base to form a compound of formula (V) and a precipitated amine salt of the base; and
b) separating the precipitated amine salt of the base from the compound of formula (V) by filtration.

[14] In another preferred embodiment, $R^1$ is $CF_3$;
$R^2$ is selected from ethene substituted with cyclopropyl and ethyne substituted with cyclopropyl;
$R^{3a}$ is H;
$R^{3b}$ is Cl;

$R^{3c}$ and $R^{3d}$ are H;
$R^{8a}$ is $CH_3$;
$R^8$ is phenyl; and
M is selected from $Li^+$ and $MgCl^+$.

[15] In another even more preferred embodiment,
the dehydrating agent is selected from methanesulfonyl chloride, thionyl chloride, acetyl chloride, and triphenylphosphine;
the amount of base is in the range of about 2 to about 7 molar equivalents and is selected from triethylamine, N-methylmorpholine, N,N-diisopropylethylamine, pyridine, 1,4-diazabicyclo[2.2.2]octane, 1,8-diazabicyclo[5.4.0]undec-7-ene, tetramethylethylenediamine, and N,N-dimethylaminopyridine; and
the suitable temperature to form the compound of formula (VII) is less than 0° C.

[16] In another preferred embodiment, the process further comprises step (3), ionizing the compound of formula (VII) to form a compound of formula (I):

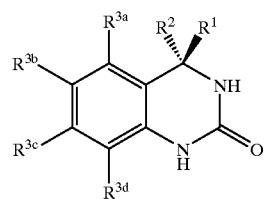

or a pharmaceutically acceptable salt form thereof.

[17] In a more preferred embodiment, step (3) comprises contacting the compound of formula (VII) with a strong acid selected from trifluoroacetic acid, formic acid, and methanesulfonic acid to form a compound of formula (I) or a pharmaceutically acceptable salt form thereof.

[18] In another preferred embodiment, the compound of formula (IV) is prepared by the process comprising:

step (1), contacting a compound of formula (II):

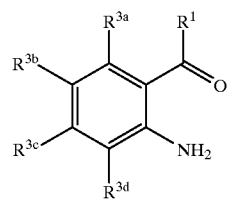

or a salt form or a hydrate of the salt form thereof;
with an isocyanate of formula (III):

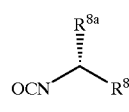

to form a compound of formula (II-a):

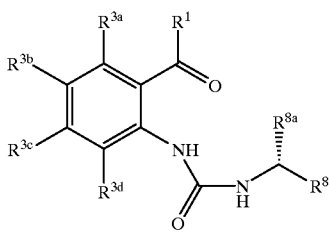

or a salt form thereof; and step (1-i), cyclizing the compound of formula (II-a) to form a compound of formula (IV).

[19] In another more preferred embodiment, $R^1$ is $CF_3$;

$R^2$ is selected from ethene substituted with cyclopropyl, and ethyne substituted with cyclopropyl;

$R^{3a}$ is H;

$R^{3b}$ is Cl;

$R^{3c}$ and $R^{3d}$ are H;

$R^{8a}$ is $CH_3$;

$R^8$ is phenyl;

M is $MgCl^+$ or $Li^+$; and the compound of formula (II) is the hydrate of the hydrochloride salt.

[20] In an even more preferred embodiment, step (1-i) comprises cyclizing the compound of formula (II-a) by heating the compound of formula (II-a) to a temperature in the range of about 50° C. to about 70° C.

[21] In another preferred embodiment, step (1) comprises contacting the compound of formula (II) with the isocyanate of formula (III) in the presence of an acid selected from hydroiodic acid, hydrobromic acid, hydrochloric acid, sulfuric acid, nitric acid, acetic acid, toluenesulfonic acid, benzene sulfonic acid, trimethylsilyl chloride, trimethylsilyl iodide, trimethylsilyl bromide, trimethyl silyl cyanide, tri-isopropylsilyl chloride, t-butyldimethylsilyl chloride, t-butyldiphenylsilyl chloride, triethylsilyl chloride, and trimethylsilyl trifluoromethanesulfonate.

[22] In a third embodiment, the present invention describes a novel process for the preparation of a compound of formula (I):

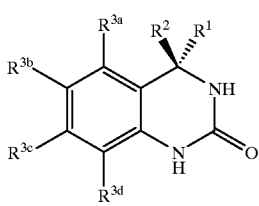

wherein:

$R^1$ is selected from $C_{1-3}$ alkyl substituted with 1–7 halogen, and $C_{2-5}$ alkynyl substituted with 1 $R^4$;

$R^2$ is selected from $CF_3$, $C_{1-5}$ alkyl substituted with 1–2 $R^4$, $C_{2-5}$ alkenyl substituted with 1–2 $R^4$, $C_{2-5}$ alkynyl substituted with 1 $R^4$, and $OR^{2a}$;

$R^{2a}$ is selected from $C_{1-4}$ alkyl;

$R^{3a}$ is H;

$R^{3b}$ is selected from H, $C_{1-4}$ alkyl, $C_{1-4}$ alkoxy, F, Cl, Br, I, and $NR^5R^{5a}$;

$R^{3c}$ is selected from H, $C_{1-4}$ alkyl, $C_{1-4}$ alkoxy, F, Cl, Br, I, and $NR^5R^{5a}$;

$R^{3d}$ is selected from H, $C_{1-4}$ alkyl, $C_{1-4}$ alkoxy, F, Cl, Br, I, and $NR^5R^{5a}$;

alternatively, $R^{3a}$ and $R^{3b}$ combine to form $-OCH_2O-$;

$R^4$ is selected from $C_{3-5}$ cycloalkyl substituted with 0–2 $R^{4a}$, phenyl substituted with 0–5 $R^{4a}$, and a 5–6 membered heterocyclic system containing 1–3 heteroatoms selected from O, N, and S, substituted with 0–2 $R^{4a}$;

$R^{4a}$ is selected from $C_{1-3}$ alkyl, Cl, Br, F, I, $OCH_3$, $SCH_3$, and $NR^5R^{5a}$; and $R^5$ and $R^{5a}$ are independently selected from H and $C_{1-3}$ alkyl;

the process comprising:

step (1), contacting a compound of formula (II):

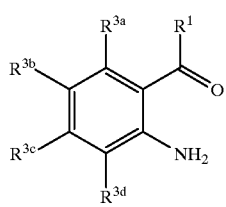

or a salt form or a hydrate of the salt form thereof;

with an isocyanate of formula (III):

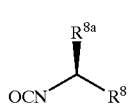

wherein:

$R^{8a}$ is selected from methyl, ethyl, propyl, and isopropyl;

$R^8$ is selected from phenyl substituted with 0–3 $R^9$, and naphthyl substituted with 0–3 $R^9$; and $R^9$ is selected from $C_{1-4}$ alkyl, $C_{1-4}$ alkoxy, F, Cl, Br, and I;

to form a compound of formula (II-a):

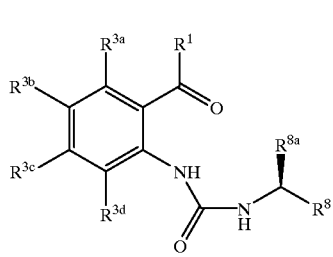

or a salt form thereof;

step (1-i), cyclizing the compound of formula (II-a) to form a compound of formula (IV):

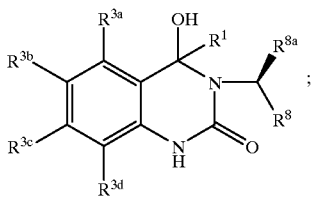

step (2), dehydrating the compound of formula (IV): to form a compound of formula (V):

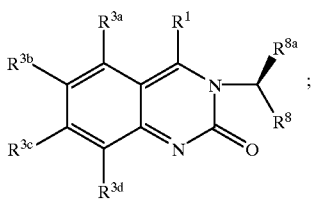

(2-i) contacting the compound of formula (V) with a nucleophile of formula (VI):

$$R^2-M \quad (VI)$$

wherein M is a metal counterion;
to form a compound of formula (VII):

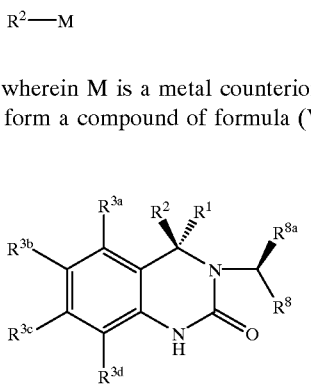

or a salt form thereof; and
step (3), ionizing the compound of formula (VII) to form a compound of formula (I), or a pharmaceutically acceptable salt form thereof.

[23] In a fourth embodiment, the present invention describes a compound of formula (IV):

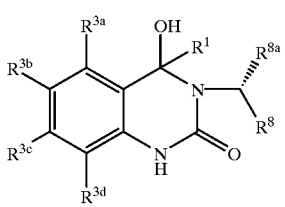

wherein:
$R^1$ is $C_{1-3}$ alkyl substituted with 1–7 halogen;
$R^2$ is selected from $C_{1-5}$ alkyl substituted with 1–2 $R^4$, $C_{2-5}$ alkenyl substituted with 1–2 $R^4$, $C_{2-5}$ alkynyl substituted with 1 $R^4$, and $OR^{2a}$;
$R^{2a}$ is selected from $C_{1-4}$ alkyl;
$R^{3a}$ is H;
$R^{3b}$ is selected from H, $C_{1-4}$ alkyl, $C_{1-4}$ alkoxy, F, Cl, Br, I, and $NR^5R^{5a}$;
$R^{3c}$ is selected from H, $C_{1-4}$ alkyl, $C_{1-4}$ alkoxy, F, Cl, Br, I, and $NR^5R^{5a}$;
$R^{3d}$ is selected from H, $C_{1-4}$ alkyl, $C_{1-4}$ alkoxy, F, Cl, Br, I, and $NR^5R^{5a}$;
alternatively, $R^{3a}$ and $R^{3b}$ combine to form —OCH$_2$O—;
$R^4$ is selected from $C_{3-5}$ cycloalkyl substituted with 0–2 $R^{4a}$, phenyl substituted with 0–5 $R^{4a}$, and a 5–6 membered heterocyclic system containing 1–3 heteroatoms selected from O, N, and S, substituted with 0–2 $R^{4a}$;
$R^{4a}$ is selected from $C_{1-3}$ alkyl, Cl, Br, F, I, OCH$_3$, SCH$_3$, and $NR^5R^{5a}$;
$R^5$ and $R^{5a}$ are independently selected from H and $C_{1-3}$ alkyl;
$R^{8a}$ is selected from methyl, ethyl, propyl, and isopropyl;
$R^8$ is selected from phenyl substituted with 0–3 $R^9$, and naphthyl substituted with 0–3 $R^9$; and
$R^9$ is selected from $C_{1-4}$ alkyl, $C_{1-4}$ alkoxy, F, Cl, Br, and I.

[24] In a fifth embodiment, the present invention describes a compound of formula (VII):

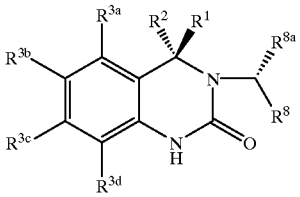

or a salt form thereof; wherein:
$R^1$ is $C_{1-3}$ alkyl substituted with 1–7 halogen;
$R^2$ is selected from $C_{1-5}$ alkyl substituted with 1–2 $R^4$, $C_{2-5}$ alkenyl substituted with 1–2 $R^4$, $C_{2-5}$ alkynyl substituted with 1 $R^4$, and $OR^{2a}$;
$R^{2a}$ is selected from $C_{1-4}$ alkyl;
$R^{3a}$ is H;
$R^{3b}$ is selected from H, $C_{1-4}$ alkyl, $C_{1-4}$ alkoxy, F, Cl, Br, I, and $NR^5R^{5a}$;
$R^{3c}$ is selected from H, $C_{1-4}$ alkyl, $C_{1-4}$ alkoxy, F, Cl, Br, I, and $NR^5R^{5a}$;
$R^{3d}$ is selected from H, $C_{1-4}$ alkyl, $C_{1-4}$ alkoxy, F, Cl, Br, I, and $NR^5R^{5a}$;
alternatively, $R^{3a}$ and $R^{3b}$ combine to form —OCH$_2$O—;
$R^4$ is selected from $C_{3-5}$ cycloalkyl substituted with 0–2 $R^{4a}$, phenyl substituted with 0–5 $R^{4a}$, and a 5–6 membered heterocyclic system containing 1–3 heteroatoms selected from O, N, and S, substituted with 0–2 $R^{4a}$;
$R^{4a}$ is selected from $C_{1-3}$ alkyl, Cl, Br, F, I, OCH$_3$, SCH$_3$, and $NR^5R^{5a}$;
$R^5$ and $R^{5a}$ are independently selected from H and $C_{1-3}$ alkyl;
$R^{8a}$ is selected from methyl, ethyl, propyl, and isopropyl;
$R^8$ is selected from phenyl substituted with 0–3 $R^9$, and naphthyl substituted with 0–3 $R^9$; and
$R^9$ is selected from $C_{1-4}$ alkyl, $C_{1-4}$ alkoxy, F, Cl, Br, and I.

[25] In a more preferred embodiment, the compound of formula (VII) is (VII-i):

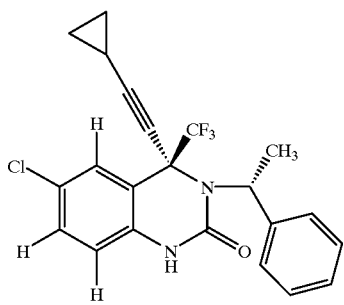

(VII-i)

or a salt form thereof.

DEFINITIONS

The following terms and abbreviations are used herein and defined as follows. The abbreviation: "THF" as used herein means tetrahydrofuran, "HPLC" as used herein means high performance liquid chromatograpy, "GC" as used herein means gas chromatography, "PCT" as used herein means process control test, "DSC" as used herein means differential scanning calorimetry, "d.e." as used herein means diastereomeric excess, "e.e." as used herein means enantiomeric excess, and "CPA" as used herein means cyclopropylacetylene.

The reactions of the synthetic methods claimed herein are carried out in suitable solvents which may be readily selected by one skilled in the art of organic synthesis, the suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction, suitable solvents for a particular reaction or work-up following the reaction may be selected. Such suitable solvents, as used herein may include, by way of example and without limitation, chlorinated solvents, hydrocarbon solvents, ether solvents, polar protic solvents and polar aprotic solvents.

Suitable halogenated solvents include, but are not limited to carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluorethane and hexafluoroethane.

Suitable hydrocarbon solvents include, but are not limited to benzene, cyclohexane, pentane, hexane, toluene, cycloheptane, methylcyclohexane, heptane, ethylbenzene, m-, o-, or p-xylene, octane, indane, and nonane.

Suitable ether solvents include, but are not limited to dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol diisopropyl ether, anisole, and t-butyl methyl ether.

Suitable polar protic solvents include, but are not limited to methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, and glycerol.

Suitable polar aprotic solvents include, but are not limited to dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile (ACN), dimethylsulfoxide, propionitrile, ethyl formate, methyl acetate, hexachloroacetone, acetone, ethyl methyl ketone, ethyl acetate, isopropyl acetate, t-butyl acetate, sulfolane, N,N-dimethylpropionamide, nitromethane, nitrobenzene, and hexamethylphosphoramide.

As used herein, "strong acid" refers to any acid having a pKa less than 4.7. These include, but are not limited to mineral acids such as hydrochloric acid, hydrobromic acid, hydroiodic acid, sulfuric acid, nitric acid, phosphoric acid; and organic acids such as formic acid, acetic acid, methanesulfonic acid, trifluoroacetic acid, propionic acid, butyric acid, valeric acid, caproic acid, oxalic acid, benzenesulfonic acid, and p-toluenesulfonic acid.

As used herein, "aqueous acid" refers to any strong acid which is soluble in water. Additionally, aqueous acid includes sodium bisulfate, potassium bisulfate, ammonium chloride, lithium bisulfate and the like.

As used herein, a "first strong acid" refers to a "strong acid" as defined above as well as a silyl agent. A silyl agent refers to a tetravalent silicon compound wherein a substituent on the silicon atom is halo, sulfonate, or a cyano group, and wherein the tetravalent silicon compound facilitates the formation of urea (II-a) in the reaction of a compound of Formula (II) with a compound of Formula (III). It is understood that a silyl agent is also a strong acid in that upon hydrolysis a silyl agent would give a pKa of less than 4.7. Silyl agents include, but are not limited to trimethylsilyl chloride (TMSCl), trimethylsilyl iodide (TMSI), trimethylsilyl bromide (TMSBr), trimethylsilyl cyanide (TMSCN), triisopropylsilyl chloride (TIPSCl), t-butyldimethylsilyl chloride (TBDMSCl), t-butyldiphenylsilyl chloride, triethylsilyl chloride, trimethylsilyl trifluoromethanesulfonate (TMSOTf), and the like.

As used herein, "base" refers to an agent, the presence of which in a dehydration reaction facilitates the synthesis of the desired product, which does not destroy the dehydrating agent, if such an agent is employed. Suitable bases may be selected by one of skill in the art of organic synthesis. Examples of such bases include, but are not limited to, organic bases such as aromatic amines such as pyridine, N,N-diethylaniline; aliphatic amines including, but not limited to, trialkyl amines such as triethylamine, N-methylmorpholine (NMM), N,N-diisopropylethylamine, N,N-diethylcyclohexylamine, N,N-dimethylcyclohexylamine, N,N,N'-triethylenediamine, N,N-dimethyloctylamine; 1,5-diazabicyclo[4.3.0]non-5-ene (DBN); 1,4-diazabicyclo[2.2.2]octane (DABCO); 1,8-diazabicyclo[5.4.0]undec-7-ene (DBU); tetramethylethylenediamine (TMEDA); and substituted pyridines such as N,N-dimethylaminopyridine (DMAP), 4-pyrrolidinopyridine, and 4-piperidinopyridine. Additionally, suitable bases can be selected from polymeric tertiary amines, as well as polymeric aromatic amines.

As used herein, "aqueous base" refers to bases which are water soluble, and useful for neutralizing aqueous acids. Examples of such bases include, but are not limited to aqueous solutions of: sodium, lithium, and potassium salts of carbonates; sodium, lithium, and potassium salts of bicarbonates; and sodium, lithium and potassium salts of hydroxides.

As used herein, "strong base" refers to any base capable of deprotonating a compound of formula $R^2$—H to give $R^2$—M, the nucleophiles of the present invention. Examples of strong bases include, but are not limited to, alkyllithiums such as isobutyllithium, n-hexyllithium, n-octyllithium, n-butyllithium, s-butyllithium, t-butyllithium, phenyllithium, and triphenylmethyllithium; metal amides such as sodium amide, potassium amide, and lithium amide; metal hydrides such as sodium hydride, potassium hydride, and lithium hydride; and metal dialkylamides such as sodium and potassium salts of methyl, ethyl, n-propyl, i-propyl, n-butyl, t-butyl, trimethylsilyl, and cyclohexyl substituted amides. Other examples of strong bases include, but are not limited to, alkyl magnesium halides and aryl magnesium halides such as, methyl magnesium chloride, ethyl magnesium chloride, propyl magnesium chloride, n-butyl-, iso-butyl-, or t-butylmagnesium chloride, pentyl magnesium chloride, hexyl mangesium chloride, and phenyl magnesium chloride. Preferred strong bases are n-butyl magnesium chloride and phenyl magnesium chloride.

As used herein, "dehydrating agent" refers to any agent capable of dehydrating a quinazolinone of formula (IV) to give a tetraene of formula (V). Such agents include, but are not limited to, sulfonyl chlorides such as thionyl chloride, methanesulfonyl chloride, ethanesulfonyl chloride, and the like; acid chlorides such as acetyl chloride, benzoyl chloride, and the like; and phosphines such as triphenyl phosphine, trimethylphosphine and the like.

As used herein, "nucleophile" refers to a nucleophilic agent of formula $R^2$—M, wherein $R^2$ is negatively charged and M is a metal counterion. Nucleophiles of the present invention are those known to be derived from $R^2$—H, and are capable of adding $R^2$ to the 4-position of a compound of formula (V). Examples include, but are not limited to, those agents known in the art of organic synthesis as Grignard reagents, cuprates, alkyl metals, and the like.

As used herein, "metal counterion" refers to a positively charged ion or complex, which serves as a pairing partner for the negative charge of the nucleophile. Examples of suitable metal counter ions include, but are not limited to positively charged ions or complexes of lithium, sodium, potassium; copper and any salts thereof, such as chloride, bromide or iodide; magnesium and any salts thereof, such as chloride, bromide or iodide; zinc and any salts thereof, such as chloride or bromide; cerium and any salts thereof, such as chloride or bromide; and calcium and any salts thereof, such as chloride or bromide. Examples of positively charged ions or complexes include $Li^+$, $Na^+$, $K^+$, $MgCl^+$, $MgBr^+$, $MgI^+$, $ZnCl^+$, $ZnBr^+$, $CaCl^+$, $CaBr^+$, $CeCl_2^+$, $CeBr_2^+$, $CuBr^+$, and $CuCl^+$.

As used herein, "ionizing" refers to the removal of the substituent, which is attached to the nitrogen in the 3-position of a quinazoline of formula (VII) through a carbon atom, by severing the C—N bond, resulting in a compound of formula (I). Conditions which affect ionization will be known to one skilled in the art of organic synthesis, and will depend upon the nature of the substituent and substrate. Examples of ionization conditions may include, but are not limited to treatment of a compound of formula (VII) with hydrogen, strong lewis acids, or bases.

As used herein, "anti-solvent" refers to any solvent which, when added to a reaction or work-up solvent, affects precipitation of the product of the reaction. By way of example, and without limitation, such antisolvents include cyclohexane, pentane, hexane, cycloheptane, toluene, methylcyclohexane, heptane, tert-butyl methyl ether, and the like.

As used herein, "crystallization solvent" refers to any solvent, which promotes the precipitation of a preferred crystalline diastereomer of the compound of formula (VII). Examples of suitable crystallization solvents include, but are not limited to alcoholic solvents such as methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, and glycerol; and polar aprotic solvents such as ethyl acetate, methyl acetate and the like; and hydrocarbon solvents such as toluene.

The compounds described herein may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention that contain asymmetrically substituted carbon atoms may be isolated in optically active or racemic forms. Methods on how to prepare optically active forms from optically active starting materials are known in the art, such as by resolution of racemic forms or by synthesis. All chiral, diastereomeric, racemic forms and all geometric isomeric forms of a structure are intended.

As used herein, "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example—$C_vF_w$, where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. "Alkenyl" is intended to include hydrocarbon chains of either a straight or branched configuration and one or more unsaturated carbon—carbon bonds which may occur in any stable point along the chain, such as ethenyl, propenyl and the like. "Alkynyl" is intended to include hydrocarbon chains of either a straight or branched configuration and one or more triple carbon—carbon bonds which may occur in any stable point along the chain, such as ethynyl, propynyl and the like.

As used herein "halo" or "halogen" refers to fluoro, chloro, bromo and iodo.

As used herein, the term "heterocycle" or "heterocyclic system" is intended to mean a stable 5- to 6-membered monocyclic heterocyclic ring which is saturated partially unsaturated or unsaturated (aromatic), and which consists of carbon atoms and from 1 to 3 heteroatoms independently selected from the group consisting of N, O and S. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 6-membered monocyclic heterocyclic aromatic ring which consists of carbon atoms and from 1 to 3 heterotams independently selected from the group consisting of N, O and S. It is preferred that the total number of S and O atoms in the aromatic heterocycle is not more than 1.

Examples of heterocycles include, but are not limited to, 2-pyrrolidonyl, 2H-pyrrolyl, 4-piperidonyl, 6H-1,2,5-thiadiazinyl, 2H,6H-1,5,2-dithiazinyl, furanyl, furazanyl, imidazolidinyl, imidazolinyl, imidazolyl, isoxazolyl, morpholinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, tetrahydrofuranyl, 6H-1,2,5-thiadiazinyl, 1,2,3-thiadiazolyl, 1,2,4-thiadiazolyl, 1,2,5-thiadiazolyl, 1,3,4-thiadiazolyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, and 1,3,4-triazolyl. Preferred heterocycles include, but are not limited to, pyridinyl, furanyl, thienyl, pyrrolyl, pyrazolyl, imidazolyl, and oxazolidinyl. Also included are fused ring and spiro compounds containing, for example, the above heterocycles.

As used herein, "stable compound" and "stable structure" are meant to indicate a compound that is sufficiently robust to survive isolation to a useful degree of purity from a reaction mixture, and formulation into an efficacious therapeutic agent. Only stable compounds are contempleted by the present invention.

As used herein, "substituted" is intended to indicate that one or more hydrogens on the atom indicated in the expression using "substituted" is replaced with a selection from the indicated group(s), provided that the indicated atom's normal valency is not exceeded, and that the substitution results in a stable compound.

The present invention includes all isotopes of atoms occurring in the intermediates or final compounds. Isotopes include those atoms having the same atomic number but different mass numbers. By way of general example and without limitation, isotopes of hydrogen include tritium and deuterium; isotopes of carbon include $^{13}C$ and $^{14}C$.

As used herein, "pharmaceutically acceptable salt" refer to derivatives of the disclosed compounds wherein the intermediates or final compound are modified by making acid or base salts of the intermediates or final compounds. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the intermediates or final compounds include the conventional non-toxic salts or the quaternary ammonium salts from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts are generally prepared by reacting the free base or acid with stoichiometric amounts or with an excess of the desired salt-forming inorganic or organic acid or base in a suitable solvent or various combinations of solvents.

The pharmaceutically acceptable salts of the acids of the intermediates or final compounds are prepared by combination with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammoinum hydroxide and the like.

As discussed above, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

The present invention is contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

The methods of the present invention may be further understood by reference to Schemes 3, 4, and 5. Scheme 3 provides the general synthesis for the compound of formula (I), and Scheme 4 provides specific conditions for the preparation of (I-i). Scheme 5 provides alternative specific conditions for the preparation of (I-i). These examples are meant to be illustrative of the present invention, and are not to be taken as limiting thereof. The synthesis of compound (II) can be accomplished by methods well known to the skilled artisan of organic synthesis, and by methods taught in commonly assigned U.S. patent application Ser. No. 09/056,820, and Tet. Lett. 1994, 35(37), 6811–6814, the disclosures of which are hereby incorporated by reference.

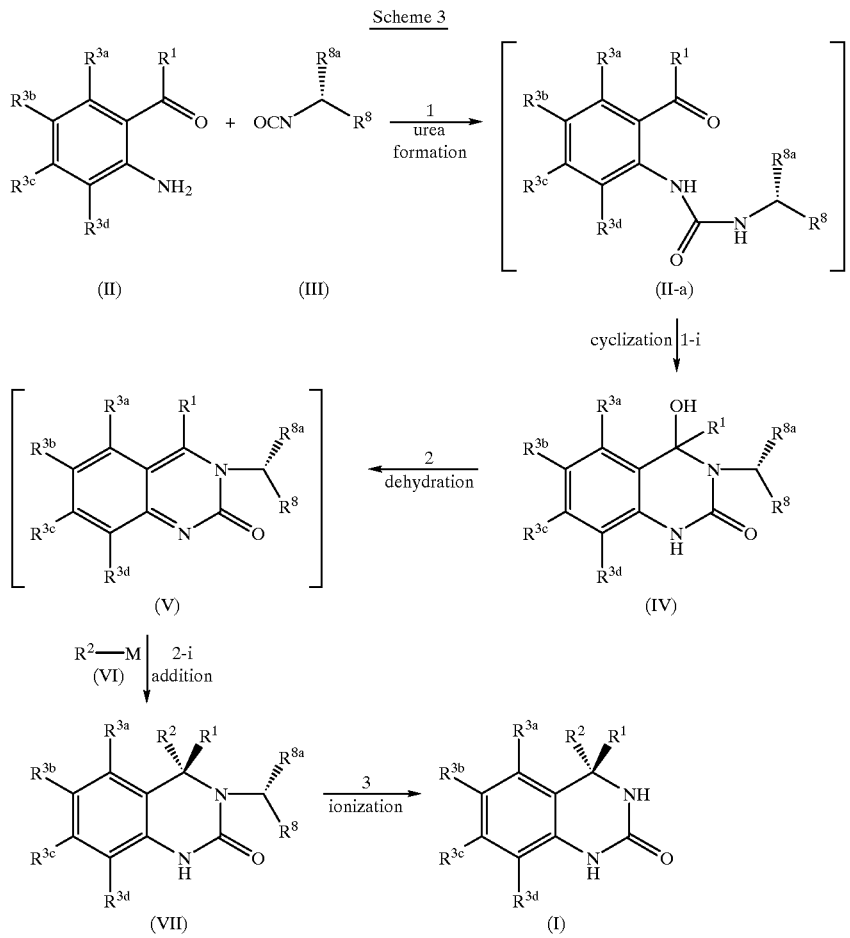

Scheme 3

SYNTHESIS

Reaction Steps (1) and (1-i): Urea Formation and Cyclization

A compound of formula (II) and a suitable solvent are preferably charged to a reaction vessel. The order of addition may be compelled by convenience, or by other process issues familiar to the artisan of process chemistry. While the reaction may be conducted in numerous solvents, tert-butyl methyl ether, acetic acid, diethoxyethane, methyl ethyl ketone, 2-methoxyethyl ether, chlorobutane, ethyleneglycol dimethyl ether, water, anisole, toluene, acetone, and tetrahydrofuran are preferred. Tetrahydrofuran is most preferred. Conditions which may facilitate the reaction include the presence of a strong acid or an aqueous acid. Preferred strong acid or aqueous acid includes mineral acids such as hydrochloric acid, hydroiodic acid, sulfuric acid, hydrobromic acid, or organic acids such as acetic acid, oxalic acid, p-toluenesulfonic acid, and benzenesulfonic acid. The acid promotes the dissolution of the hydrate form or halo-hydrin form of the ketone, which is typically the more reactive form of this class of compounds. If an acid is employed, the most preferred combination of acid and solvent is about 1N HCl in tetrahydrofuran, which is charged in the range of about 1% to about 25% of the solvent volume. More preferred is about 3% to about 7% of the solvent volume. If the following isocyanate addition is done rapidly, an exotherm will be produced accompanied by the evolution of carbon dioxide, but the gas release is generally mild.

An isocyanate is preferably added to the vessel in an amount of about 1 to about 3 equivalents based on compound (II). A more preferred amount of isocyanate is about 1.9 to about 2.1 equivalents. It may be advantageous to monitor the temperature during the addition. If the pot temperature rises above ambient before the isocyanate is consumed, undesired by-products typically form.

The formation of compound (II-a) is preferably done at a temperature in the range of about 0° C. to the boiling point of the solvent employed. A more preferred temperature range is from about 0° C. to about 20° C., which tends to retard side reactions, including the decomposition of the isocyanate to a symmetrical urea by-product.

The reaction is preferably monitored by HPLC, and is considered complete when the isocyanate peak is about <1% by area. Depending on the solvent and temperature conditions chosen, the reaction takes from about 15 to about 72 hours. Under the preferred conditions, the reaction is usually complete after about 15 to about 20 hours. The preferred temperature range is typically maintained throughout the reaction to avoid the production of the aforementioned symmetric urea by-product. Preferably, the amount of this by-product is <1% by area as determined by HPLC.

Following the formation of (II-a), conversion to (IV) takes place via cyclization. The cyclization is preferably accomplished by allowing the mixture to age under conditions similar to those employed for the formation of (II-a). Temperatures appropriate for the cyclization are those which lead to the formation of (IV), preferably in the range of about 0° C. to about 200° C. The reaction rate is more preferably increased by heating the compound of formula (II-a) to a temperature in the range of about 40° C. to about 70° C. The most preferred temperature for completing the reaction is about 55° C. to about 65° C. By way of example, cyclization will generally be complete after about 1 to about 2 hours if the reaciton solution containing (II-a) is heated at about 60° C. The cyclization may be monitored by HPLC, with completion evidenced by sufficient consumption of (II-a).

After the reaction is complete, the acid salts of the amines generated may be removed from the crude reaction mixture by washing the reaction solution with water. The product is preferably crystallized by exchanging the reaction solvent with an anti-solvent, which will affect the precipitation of the product. Preferred antisolvents include hydrocarbons such as pentane, heptanes, hexanes and toluene; and ethers such as diethyl ether and tert-butyl methyl ether. More preferred is the use of toluene or heptanes as the antisolvent. Most preferred is the use of heptanes as the antisolvent. The preferred final percentage of anti-solvent after solvent exchange is at least 99% by volume as judged by gas chromatography (GC); more preferred is at least 99.5% by volume of the anti-solvent as judged by gas chromatograph (GC), conditions for which will be readily understood by one skilled in the art. The product is isolated, preferably by filtration, and may be washed with additional anti-solvent. The product is preferably dried under vacuum at about 70° C. to a constant weight.

An alternative method of preparing a compound of Formula (IV) will now be described. A compound of Formula (II) and a suitable solvent are preferably charged to a reaction vessel. The order of addition may be compelled by convenience, or by other process issues familiar to the artisan of process chemistry. A wide variety of organic solvents can be implemented in this procedure. These solvents include, but are not limited to, ethers such as tert-butyl methyl ether, diethyl ether, diisopropyl ether, butyl ether, diethoxyethane, 2-methoxyethyl ether, ethylene glycol dimethyl ether, and tetrahydrofuran; aromatic solvents such as benzene, methoxybenzene, ethoxybenzene, o-, m-, or p-xylene, and toluene; halogenated solvents such dichloromethane, 1,2-dichloroethane, chlorobutane, and chlorobenzene; alcohols such as methanol, ethanol, propanol, butyl alcohol, isopropanol, s-butyl alcohol, and pentanol; and hydrocarbons such as pentane, hexanes and heptanes. These specific solvents are listed by example only, many other solvents can also be used. The reaction is also effective in a binary, tertiary or a multiple combination of organic solvents. For example, when the reaction is run in the binary solvent system of tetrahydrofuran and heptane, the product crystallizes out of solution upon completion of the reaction due to the insolubility of the product. A variety of acids such as mineral acids, alkyl- or arylsulfonic acids, or carboxylic acids facillitate this reaction. The mineral acids include, but are not limited to, hydroiodic acid, hydrobromic acid, hydrochloric acid, sulfuric acid; the alkylsulfonic and arylsulfonic acids include, but are not limited to, methanesulfonic acid, p-toluenesulfonic acid, trifluoromethane sulfonic acid; and the carboxylic acids include, but are not limited to, acetic acid, trifluoroacetic acid, propionic acid, butyric acid, valeric acid, and caproic acid.

Besides the above acids, a silyl agent acting as a strong acid can be used to facillitate step (1), the urea formation, to give a compound of formula (II-a). An advantage for using a silyl agent acting as a strong acid for the urea formation is that the number of equivalents of isocyanate for a complete conversion of compound (II) is reduced since the reaction is run under anhydrous conditions. Under the anhydrous conditions, a silyl agent is more preferred than a mineral acid or an organic acid for facillitating the urea formation to give adduct (II-a). A silyl chloride agent may facillitate the urea formation by reacting with the $NH_2$ amine group to release hydrochloric acid HCl. The silyl agent may also complex with the isocyanate (III) resulting in the activation of the isocyanate (III) for the reaction with compound (II). Silyl agents include TMSCl, TMSI, TMSBr, TMSCN, TIPSCl, t-butyldimethylsilyl chloride, triethylsilyl chloride, and trimethylsilyl trifluoromethanesulfonate. The preferred silyl agents are trimethylsilyl chloride, trimethyl silyl bromide, trimethylsilyl iodide, triethylsilyl chloride, and trimethylsilyl trifluoromethanesulfonate. The most preferred silyl agent is trimethylsilyl chloride. The preferred amount of equivalents of a silyl agent is 0.2 equivalents to 1.5 equivalents. The most preferred amount of equivalents of a silyl agent is 0.2 equivalents.

The preferred anhydrous solvents for this alternative method are tetrahydrofuran, t-butyl methyl ether, diethyl ether, ethylene glycol dimethyl ether, ethylene glycol diethyl ether, diethylene glycol dimethyl ether, diethylene glycol diethyl ether, diisopropyl ether, toluene, chlorobutane, chlorobenzene, chlorotoluene, m-, o-, or p-xylene, cyclohexane, hexanes, heptane, cycloheptane, octane, indane, and nonane.

The preferred binary solvent system involves a combination of tetrahydrofuran and toluene, tetrahydrofuran and xylenes, t-butyl methyl ether and toluene, t-butyl methyl ether and xylenes. The more preferred binary solvent system is tetrahydrofuran and toluene. When trimethylsilyl chloride is used as the acid, only a catalytic amount is needed, about 20 mole percent. A greater amount, about one equivalent, can be used without slowing the reaction rate.

An isocyanate is preferably added to the vessel in an amount of about one to about three equivalents based on compound (II). When the reaction is run under anhydrous conditions, a more preferred amount of only one equivalent of isocyanate is necessary for the complete conversion. Permutations in the sequential addition of the reagents in the reaction do not affect the overall outcome.

The reaction of compound (II) is preferably done at a temperature where compound (II) is soluble to the boiling point of the solvent system. The preferred temperature for the reaction is below 50° C. in order to reduce the amount of by-products that are formed in the reaction. A more preferred temperature for the reaction is −20° C. to 50° C. An even more preferred temperature is 20–50° C. The reaction is usually complete after approximately 14 hours at 35–45° C. Depending on the specific reaction conditions chosen, the reaction could take from 2 to 72 hours. Under the preferred conditions, the concentration of starting material in tetrahydrofuran is 1 mL/g or with toluene is 3–4 mL/g.

The intermediate (II-a) is formed during the reaction, but the intermediate is never isolated. It undergoes cyclization under the reaction conditions to give the compound (IV). The preferred temperature for cyclization is about −40° C. to about 70° C.

The reaction is monitored by HPLC and the completeness of the reaction is determined by the consumption of the peak for compound (II) and the isocyanate. Whenever the peak for compound (II) is <1.5 A % or the peak for the isocyanate is <1 A %, the reaction is considered complete. When the reaction is complete, the product is crystallized by exchanging some or all of the reaction solvent for heptanes. The preferred final percentage of THF after solvent exchange is less than 1%, and the preferred final percentage of toluene is less than 1% to about 80%.

Reaction Steps (2) and (2-i): Dehydration and Addition

A quinazolinone of formula (IV) and a suitable solvent are preferably charged to a reaction vessel. The charging is preferably followed by an excess of a base with respect to the quinazolinone. Acceptable solvents include those which are unreactive to the dehydrating agents. While the reaction may be conducted in numerous solvents, tetrahydrofuran, toluene, acetonitrile, and tert-butyl methyl ether are preferred. More preferred is tetrahydrofuran and toluene. Most preferred is toluene. Acceptable bases include those which are unreactive to the dehydrating agents. Examples of such bases include, but are not limited to, tertiary amines. Preferred tertiary amines include N,N-diisopropylethylamine, triethylamine, N-methylmorpholine, DABCO, DBU and DMAP. Most preferred is triethylamine or N-methylmorpholine. The number of equivalents of base will depend upon the reaction conditions. For example, if the dehydrating agent generates residual acid, additional amine may be necessary to reach reaction completion. Further, the use of base may aid in the dissolution of compound (IV). Such concerns will be readily understood by one skilled in the art. Preferred amounts of amine, however, include about two to about ten equivalents based on the molar equivalents of (IV). More preferred is about two to about seven equivalents. Most preferred is about 2 to about 6 equivalents.

The reaction mixture may be cooled and a dehydrating agent added. The temperature is preferably in the range of about 10° C. to about −78° C. during the addition of the dehydrating agent. More preferred is about 0° C. to about −20° C. Dehydrating agents include those which affect the formation of (V) including, but not limited to, acid chlorides, sulfonyl chlorides, and phosphines. Preferred dehydrating agents include acetyl chloride, benzoyl chloride, methanesulfonyl chloride, ethanesulfonyl chloride, benzenesulfonyl chloride, thionyl chloride, triphenyl phosphine, and trimethyl phosphine. More preferred dehydrating agents are thionyl chloride and methanesulfonyl chloride. Most preferred is thionyl chloride. The preferred number of equivalents of dehydrating agent is greater than one based on compound (IV). More preferred is about one to about three equivalents.

The reaction is preferably allowed to age or stir until the reaction is judged complete. Reaction completion may be monitored continuously by quenching an aliquot of the reaction mixture with an alcohol, preferably methanol, and subjecting the resulting solution to HPLC analysis. Formation of (V) will be indicated by the presence of the corresponding methoxyhemiaminal analog. The formation of (V) is considered complete when HPLC analysis reveals >90% methoxyhemiaminal by area upon quench, when compared to the starting material (IV). More preferred is >93% by area. Most preferred is >95% by area.

The nucleophile is preferably prepared separately and added to the vessel containing compound (V). The nucleophiles of the present invention include those known in the art to be commercially available. Otherwise, generation of the nucleophile may be accomplished by the deprotonation of $R^2$—H. Deprotonation is typically accomplished by contacting $R^2$—H with a strong base, in a suitable solvent to result in a nucleophile of the form $R^2$— M, wherein M is a metal counterion. The pKa of $R^2$—H will depend on the nature of $R^2$, and as such, may call for the judicious choice of a strong base for deprotonation. The choice of the base will be readily understood by one skilled in the art. Deprotonation will likely be exothermic. Therefore, temperatures such as those below about 40° C. are preferably employed during addition of the strong base to $R^2$—H. The same well known methods in the art may be employed to generate the Grignard or cuprate derivative of $R^2$—H. Further guidance on the generation of alkyl metals, including Grignard and cuprate reagents can be found in Advanced Organic Chemistry, March, 4th Ed., John Wiley and Sons, Inc., 1992, a common text in the field.

The metal counterion is typically derived from the agent used to deprotonate $R^2$—H. Preferred metal counter ions include those which traditionally result from the preparation of a Grignard reagent such as magnesium halides, wherein the halide is preferably bromine, iodine, or chlorine ($MgBr^+$, $MgI^+$, $MgCl^+$). Other preferred metal counterions may be those resulting from the preparation of alkyl metal nucleophiles, such as lithium ($Li^+$), sodium ($Na^+$), potassium ($K^+$), and the like. The more preferred metal counter ions are lithium ($Li^+$) and magnesium chloride ($MgCl^+$). Most preferred is magnesium chloride ($MgCl^+$).

It will be readily understood to one skilled in the art that the temperature and rate at which the addition takes place will likely affect the diastereoselectivity of the reaction. In order to exemplify methods that maximize diastereoselectivity and reaction rate, preferred temperatures are set forth. The present invention, however, includes all temperatures at which the addition is feasible, that is conditions under which any degree of desired diastereoselectivity is achieved. Preferred reaction conditions are those which result in a diastereomeric ratio of 80:20 or higher for the desired and undesired diastereomers, respectively. More preferred is a ratio of 90:10, with 95:5 being most preferred. Addition of the nucleophile generally takes place at a suitable temperature in the range of about 0° C. to about −70° C. More preferred is about −50° C. to about −70° C. At the preferred temperatures, the reaction takes about 0.5 to about 5 hours to reach completion, but typically <1 hour.

The reaction may be quenched at a temperature in the range of about 0° C. to −70° C. with a suitable aqueous acid. Preferred aqueous acids include citric acid, acetic acid, hydrochloric acid, sulfuric acid, phosphoric acid, nitric acid and sodium bisulfate. Most preferred is citric acid. Additional solvent may be added to help discern the aqueous and organic layers.

The aqueous and organic phases are preferably separated and the organic phase concentrated. The reaction solvent is preferably exchanged for a crystallization solvent which causes a single diastereomer of (VII) to crystallize. Preferred crystallization solvents include alcohols such as methanol, ethanol, propanol, isopropanol and mixtures of these alcohols with an antisolvent. Preferred antisolvents include toluene and tert-butyl methyl ether. The most preferred crystallization solvent is a methanol/toluene mixture having a concentration of about 2% to about 20% toluene in methanol. The crystallization may also be accomplished by exchange of the reaction solvents with an antisolvent, followed by a reslurry of the isolated product in a crystallization solvent. Typically this will improve product purity. Compound (VII) is isolated, preferably by filtration, and may be rinsed with an antisolvent. The product is preferably dried under vacuum preferably at a temperature in the range of about 30° C. to 50° C., to a constant weight.

An alternative method for the preparation of compound (VII) will now be described. The previous procedure for preparation of compound (V) is used with the following changes. The base for the dehydration step is N-methylmorpholine. The preferred amount of base is 2.5 equivalenets based in the molar equivalents of (IV). Also after the formation of compound (V) has been judged to be complete, additional N-methylmorpholine base is added to the reaction to precipitate the amine salt. Again the preferred amount of additional base is about 2.5 equivalents based on the molar equivalents of (IV). After addition of the base the precipitated amine salt is separated from the mother liquor. Methods of separation are well known in the art. It is preferred that the precipitated amine salt is removed by filtration. It is understood that filtration can be by gravity, vacuum or under positive pressure. It is more preferred that the precipitated amine salt is removed by filtration under an anhydrous condition and under an atmosphere of an inert gas such as nitrogen or argon. The filtrate containing compound (V) is collected in a vessel for the addition step (2-i). Alternatively, separation of compound (V) can be obtained by decanting the supernatant from the precipitated amine salt.

In this alternative method the addition step (2-i) of the previous procedure is used, however a lesser number of equivalents, about 1 to 2.5 equivalents, of compound $R^2$—M (VI) can be used, because the removal of the precipitated N-methylmorpholine salt eliminates the need for additional equivalents of $R^2$—M (VI). The procedure for work-up and isolation of compound (VII) is not changed as previously described.

Reaction Step (3): Ionization

A quinazoline of structure (VII) and a strong acid are preferably charged to a reaction vessel. While numerous strong acids may be used, those with a pKa of <4.7 are preferred. Examples of such preferred acids include hydrochloric acid, nitric acid, sulfuric acid, phosphoric acid, formic acid, trifluoroacetic acid and methanesulfonic acid. Trifluoroacetic acid and formic acid are the most preferred. In addition to the use of strong acids to affect ionization, additional acids such as sulfonic based acids and carboxylic acids can be added to act as the solvent and/or solvolysis agent. The volume of acid is typically based on the weight of compound (VII), and is preferably about 1 mL per gram to about 10 mL per gram. More preferred is about 3 mL per gram to about 7 mL per gram. In some cases additional solvents may also be added to enhance the rate of ionization. Preferred solvents for this purpose include water, methanol, ethanol, isopropanol, dichloromethane, chloroform, thioanisole, chlorobutane, anisole, thiophenol, triethylsilane, poly(methylhydrosilane), and acetonitrile. Water is the most preferred solvent for this purpose.

The reaction is typically carried out at temperatures in the range of about −20° C. to about 150° C. The preferred temperature range is about 0° C. to about 100° C. More preferred is about 0° C. to about 70° C. At suitable temperatures, the reaction is usually complete after about 0.25 to about 20 hours. The preferred temperatures provide the product after about 1 to about 3 hours. Reaction completion is preferably determined by HPLC. Under preferred conditions, the conversion of (VII) to (I) is >99% by area at completion (or <1% starting material).

The product may be worked-up by methods familiar to one skilled in the art. Suitable techniques include the addition of a solvent to the reaction mixture followed by the neutralization of the strong acid with an aqueous base.

Suitable aqueous bases include aqueous solutions of: sodium, lithium, and potassium carbonates; sodium, lithium, and potassium bicarbonates; and sodium, lithium and potassium hydroxides. Preferred bases are those which do not generate carbon dioxide upon neutralization. Sodium hydroxide is most preferred.

Alternatively, the acid may be removed by extraction of the reaction mixture with water, which is preferred. The reaction mixture is preferably diluted by the addition of water and a solvent suitable for work-up. The amount of additional water and solvent needed will be readily understood by one skilled in the art. By way of example, water may be added in an amount in the range of about 1 mL per gram (VII) to about 10 mL per gram (VII). More preferred is about 3 mL per gram to about 7 mL per gram.

As mentioned, an additional solvent may be added to assist in the extraction. Preferred solvents for this purpose include toluene, heptane, hexane, pentane, methyl acetate, ethyl acetate, chloroform, methylene chloride, chlorobutane and xylenes. The most preferred solvent is toluene, which has been found to solubilize various reaction impurities. The preferred amount of toluene is about 1 mL per gram (VII) to about 10 mL per gram (VII). More preferred is about 3 mL per gram to about 7 mL per gram.

The aqueous and organic phases are preferably contacted by stirring the mixture vigorously. The pH of the aqueous phase may be monitored to assure adequate removal of acid. Preferably, the pH is about 2 or less. The aqueous phase may be drained and replaced with fresh water and the extraction procedure repeated until the desired pH is obtained.

The product may be precipitated by concentrating the organic phase, preferably by distillation. Precipitation may be assisted by the addition of an anti-solvent, and distilling to a predetermined solvent composition. Preferred anti-solvents include heptane, hexane, and pentane. Addition of the anti-solvent is preferably accompanied by continued removal of solvent by distillation until <5% of the solvent added for the work-up remains, as evidenced by GC analysis. The mixture is preferably cooled to afford a slurry.

The product is isolated, preferably by filtration of the slurry, and washed with additional anti-solvent. Preferred anti-solvents for washing include heptanes, hexanes, and pentane. Most preferred is heptane. The solids may be dried under vacuum at about 60° C. to about 130° C. to a constant weight.

Alternatively, an alcoholic anti-solvent such as methanol, ethanol, isopropanol, and the like may be employed if the alcoholic solvate of the final product is desired. In this case, the isolated solids are preferably heated to about 85° C. to about 100° C. for about 1 to about 3 hours, followed by heating at about 115° C. to 125° C. for an additional about 1 to about 3 hours to remove the alcohol and form crystalline Compound (I). These solids may be monitored by DSC and XRD to assure formation of the thermodynamic polymorph of the product.

Scheme 4
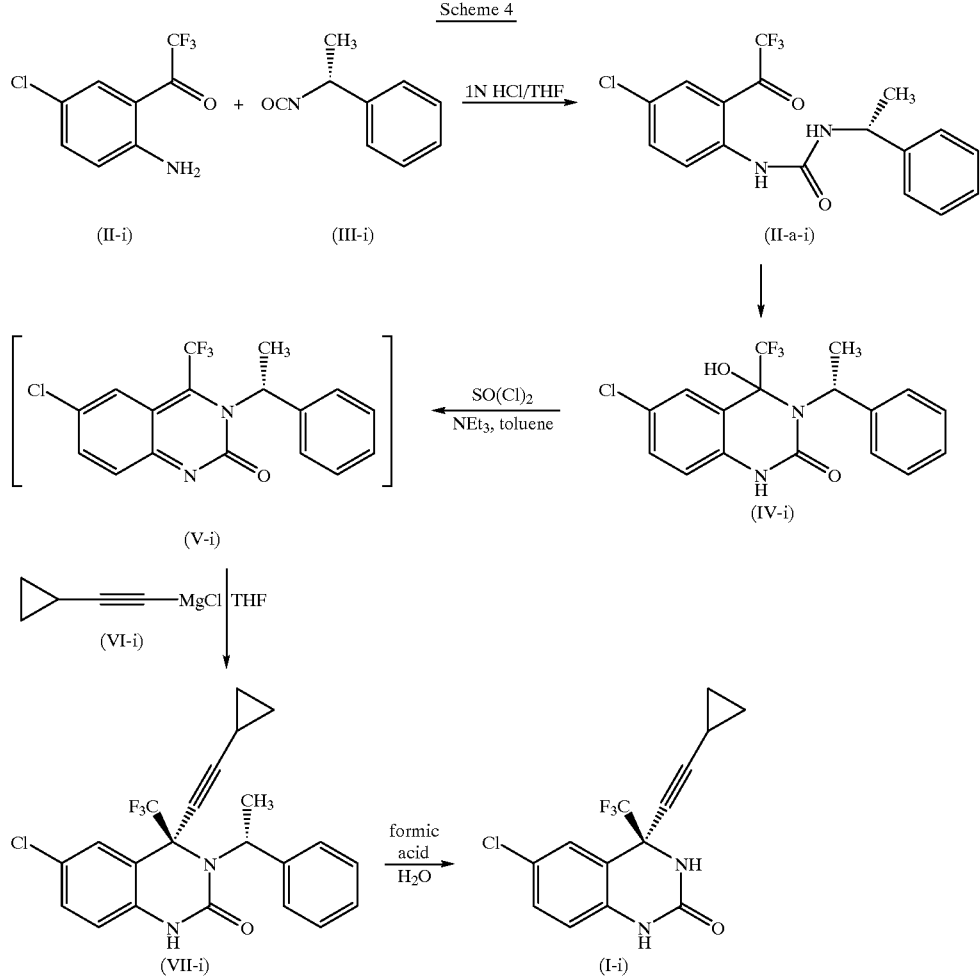
Scheme 5
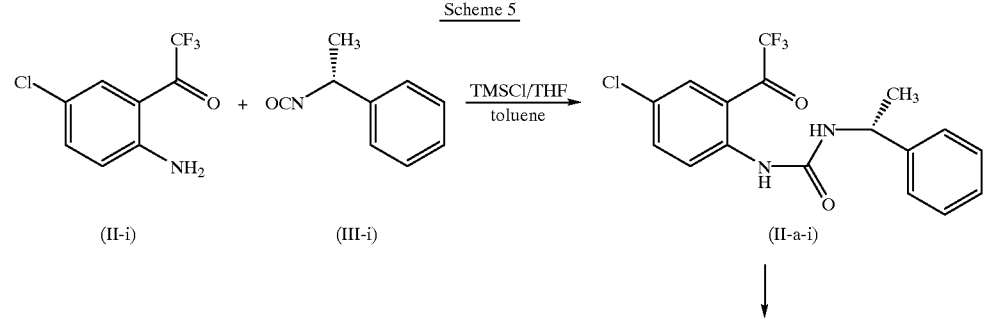

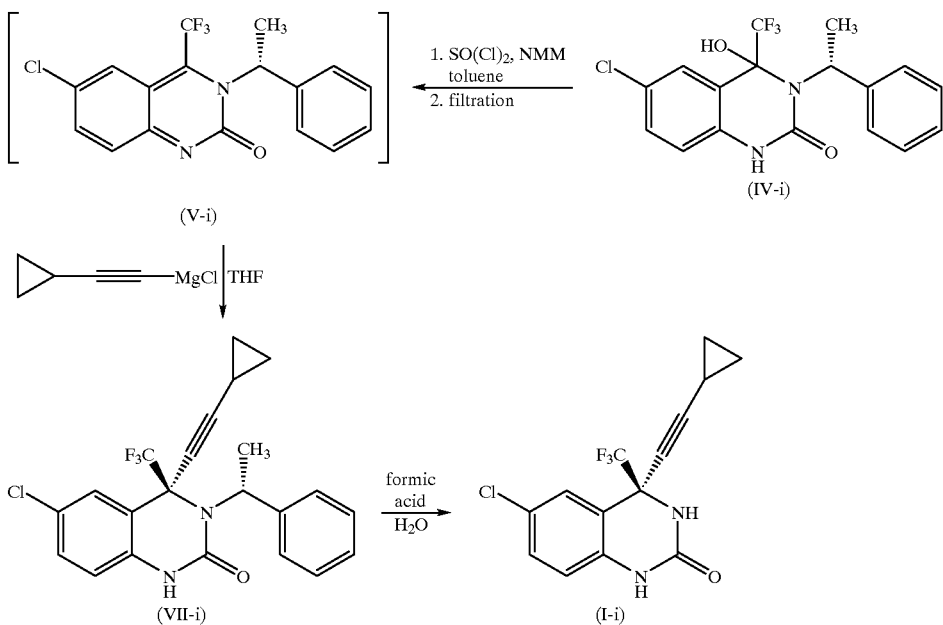

EXAMPLES

Preparation of Quinazolinone (IV-i) from Ketone (II-i) (Scheme 4)

A 100 gallon reactor was charged with solid (II-i) as its hydrochloride hydrate (21 kg, 75.51 moles) followed by THF (93 kg), water (7 kg), and 37% HCl (0.72 kg). The mixture was stirred until homogeneous at ambient temperature (0.5 h) and cooled to between 0 and 5° C. Neat (R)-(+)-α-methylbenzyl isocyanate (22.2 kg, 150.83 moles) was added to the reaction mixture over 1 to 2 hours while maintaining an internal temperature of 0 to 5° C. throughout the addition. Immediately after the isocyanate addition, the jacket temperature was increased to roughly 10 to 15° C. for 3 hours (mild gas evolution was constant). The jacket temperature was increased to roughly 15° C. and held for 15 to 20 hours. Intermediate conversion checks (A % by HPLC) are made based on consumption of isocyanate. After complete isocyanate consumption (<1 A % at 215 nm by HPLC), the temperature is increased to between 60 to 65° C. for about 2 hours, until acyclic urea (II-a-i) is no longer detected by HPLC. The reaction is cooled to about 20° C.

PCT (process control test): A sample was taken from the vessel to obtain in-process information. The weight percent of (II-i) and (VI-i) is determined by HPLC. When conversion was deemed sufficient, the reaction was quenched.

Water (53 L) was added to the reaction mixture followed by toluene (36 kg), and the mixture was stirred for 0.5 hours. After holding for 0.5 hours, the phases were separated. The organic layer was washed with water (53 L) (mix for 0.5 h, let sit about 0.5 h), and the phases separated.

Toluene (55 kg) was added to the organic phase at roughly 20° C. The solvent distilled off under reduced pressure (55 to 65° C.) to remove roughly 180 kg of distillate. An additional amount of toluene (180 kg) was charged to the reactor, and roughly 112 kg of solvent is distilled off under reduced pressure (55 to 65° C.). GC analysis indicated less than 0.17% THF in the vessel. The resulting mixture was cooled (0 to 5° C.) slowly (1 to 2 h) to induce precipitation of the desired product (IV-i). The wt. % of (IV-i) in the supernatant was monitored until constant (roughly 2%).

The product was filtered, rinsed with cold (0 to 5° C.) toluene (100 kg), and dried in a vacuum oven (at least 50 mm Hg vacuum, 70 to 90° C.) until constant weight was acheived (15 to 20 h). The product was isolated as a white to light yellow crystalline solid. $^1$H NMR (300 MHz; D$_6$-dmso) δ 9.90 (s, 1H), 8.80 (s, 1H), 7.50 (bs, 1H), 7.45 (dd, J=2.3, 8.4 Hz, 1H), 7.39–7.36 (m, 2H), 7.28–7.23 (t, J=7.6 Hz, 2H), 7.18–7.13 (m, 1H), 6.93 (d, J=8.8 Hz, 1H), 5.24 (q, J=6.8 Hz, 1H), 1.86 (d, J=6.8 Hz, 3H). $^{19}$F NMR (282 MHz, D$_6$-dmso) d −81.8 (s). $^{13}$C NMR (75 MHz, D$_6$-dmso) δ 17.9, 50.4, 84.7 (q, J=30 Hz), 115.8, 117.0, 124.0 (q, J=290 Hz), 124.9, 126.3, 127.0, 127.9, 131.6, 136.0, 143.3, 150.2; IR (KBr) 3408, 3060, 2931, 2834, 1658, and 1607 cm$^{-1}$; HRMS (CI; M+1) calcd. for C$_{17}$H$_{14}$ClF$_3$N$_2$O$_2$ 371.0774. Found: 371.0764. [a]$^{25}_D$+195° (c=1.00, EtOAc). Anal. Calcd. for C, 55.07; H, 3.81; N, 7.56. Found: C, 55.33; H, 3.80; N, 7.51; DSC 240 to 250° C. decomposition.

Alternative Method for the Preparation of Quinazolinone (IV-i) from Ketone (II-i) (Scheme 5)

In a 22 L four-neck round bottom flask/reactor equipped with mechanical stirrer, an internal thermocouple probe, and nitrogen adapter, the following materials are charged: 6 L of deionized water and 616 grams of sodium acetate (7.5 moles). When a homogeneous solution appears, the hydrated hydrochloride salt of (II) (1.244 kg, 4.47 moles) and toluene (5 L) are added to the reactor portionwise. Once all the materials have been added, a heating apparatus is attached to the reactor as the vigorously stirring solution is gently warmed to 35° C. The yellow color will eventually fade into a dark orange color over the period of time. When the orange color appears homogeneous, which is usually around 60 to 80 minutes, the heating apparatus is turned off to let the solution cool or equilibrate to room temperature.

The lower yellow aqueous layer is separated from the organic orange layer via draining or siphoning out of the reactor. The organic layer is then briefly washed with water (5 L or more). Depending on the amount of the water present in the solution by Karl Fischer (KF), an additional 3 to 5 L of toluene is added to the reaction. The solution is then concentrated to leave 5 L of toluene (the original volume).

The distillation can take place at room temperature (92–110° C.) or at reduced pressure (40 to 50 mmHg, 40–50° C.). Once the removal of water as an azeotrope is complete by KF<600 ppm, then under nitrogen, 1 L of THF is added to the reaction. The compound (II-i) is then used for the subsequent step.

The same 22 L reactor in which the free base was done now contains THF (1 L), toluene (5 L), and compound (II-i)(1 Kg, 4.47 moles). Taking into account the free base content of compound (II-i) lot, which is determined by Wt % assay and which varies from one lot to another, the following reagents should be estimated accordingly to the amount of free base that is present in the reaction. A catalytic amount (20 mole %) of TMSCl (113 mL) is required and charged into the reaction. Finally, 1 equivalent of neat (R)-(+)-α-methylbenzyl isocyanate (0.67 L, 4.7 moles) is added to the reaction mixture at room temperature over a period of 5 minutes or less. After the isocyanate addition, the mixture is heated to a temperature of about 35 to 45° C. When the optimum temperature is reached, a period of 12–14 hours is required and then intermediate conversion checks (A % by HPLC) are made every hour based on the consumption of compound (II-i) at 245 nm. More frequent checks should be made when there is <3 A % at 245 nm by HPLC. While checking the A % by HPLC, all the other peaks should be excluded from the final area integration leaving the starting material and product peaks. Once <1.5 A % of (II-i) at 245 nm by HPLC or <1.0 A % of isocyanate at 215 nm, the reactor can be prepared to perform a solvent exchange. Solvent exchange is done by adding heptane (12 L) over a half hour to the reaction while the temperature remains the same (63 to 68° C.) and the solvent is distilled off at atmospheric pressure until the pot volume is around 5 L. GC should indicate less than 1 volume % THF in the pot. If not, add an additional 5 L of heptane and resume distillation until the previous pot volume is reached. The resulting mixture is cooled (0 to 5° C.) slowly (1 to 3 hr) to induce precipitation of the desired compound (IV-i). The wt % of (IV-i) in the supernatant should be monitored until constant (typical wt % is <1.6%). The product (IV-i) is filtered, rinsed with cold (0 to 5C) heptane (3 L) and the cake dimensions measured. The compound (IV-i) is dried in a vacuum oven (25 mm Hg, 70° C.) with an $N_2$ sweep for 15 to 20 hrs or until constant weight. The product (IV-i) is isolated as a white to light yellow crystalline solid (M.p. 248–250° C.). PCT: check final purity (typical values: 100 A %, 100 wt %, KF=0.11 ppm).

Preparation of Quinazoline (VII-i) from Quinazolinone (IV-i) (Scheme 4)

A vessel was charged with 2M n-Butylmagnesium chloride in THF (three to four equivalents relative to (IV-i)) and a 5% molar excess of cyclopropylacetylene (CPA) was added over 1–3 hours at a reaction temperature of 30–40° C. in order to form a 2M solution of CPA-MgCl. Butane was allowed to escape through a condenser set at 0–5° C. After addition was complete the reaction was allowed to age for 2–3 hours at 35° C., followed by cooling to 20° C.

A low temperature reactor was charged with (IV-i) (8 kg, 21.58 moles), toluene (80 L; 10 L per kg (IV-i)) and triethylamine (10.9 kg, 107.72 moles; five equivalents relative to (IV-i)) at 20° C. The solution was cooled to between −20 to −5° C. and thionyl chloride (2.7 kg, 22.69 moles; 1.05 mole per mole of (IV-i)) was added over 1–2 hours. The deep orange mixture was aged for 1 hour at −5 to 0° C., and cooled to −50° C.

The 2M CPA-MgCl solution was added to the tetraene (V-a-i) solution over 2 to 4 h, keeping the reaction temperature below −50° C. Little product formed during the first two thirds of the addition as salts were neutralized. After about a 1 hour age period, a sample was quenched into methanol and the percent conversion to products measured by HPLC.

The reaction solution was transferred to a larger vessel containing a 12% solution of citric acid in water (enough to neutralize the base equivalents) at 20° C. The addition rate of the cold reaction to the quench mixture was controlled to keep the water from freezing. The temperature was raised from 0 to 20° C., and the layers separated. Water was added and the resulting mixture stirred for 0.5 hours, and the layers separated. The aqueous layers contained only traces of product and had a pH of 5 to 7. The organic layer was concentrated by distillation to 30% of its starting volume, which removed CPA, THF, water, and most of the toluene. During this distillation the product began to crystallize. Methanol was added over 1–3 hours while distilling the toluene-methanol azeotrope to half the starting volume, and a solvent composition of about 2% toluene-methanol. For convenience, the methanol for the solvent exchange was added in two portions. The slurry was cooled slowly from 63 to 20° C., and the concentration of (VII-i) in the supernatent analyzed. The slurry was cooled further to 5° C. over 1–3 hours, aged for 1 hour, and filtered. The product was rinsed with cold methanol and dried in a vacuum oven at 40–45° C. to give 7.7 kg (VII-i) in about 85% yield. The product was >99% pure and contained only traces of diastereomer, enantiomer, and pentenyne analogs. CHN Found: C, 63.31; H, 4.31; N, 6.70; mp 212° C.; ES+MS: M+1 419/421, 3:1; UV 253 nm; IR (KBr) 3190, 3058, 2941, 2240, 1683, 1604, 1502 $cm^{-1}$; $^1H$ NMR (300 MHz; $D_6$-dmso) δ 10.05 (s, 1H), 7.49 (s, 1H), 7.49 (d, J=9.1 Hz, 1H), 7.29 (m, 4H), 7.18 (m, 1H), 6.97 (d, J=9.1 Hz, 1H), 5.38 (bs, 1H), 1.77 (d, J=6.8 Hz, 3H), 1.62 (bs, 1H), 0.94 (m, 2H), 0.75 (bs, 2H);. $^{19}F$ NMR (282 MHz; $D_6$-dmso) d −78.4 (S); $^{13}C$ NMR (75 MHz; $D_6$-dmso) δ −1.2, 8.3, 8.4, 19.8, 57.4(br), 64.6 (q, br), 66.2, 96.0, 115.0, 115.8, 123.8 (q, J=290 Hz), 125.0, 125.7, 125.8, 127.6, 127.9, 131.2, 136.2, 141.9, 150.0.

Analytical Methods for the Preparation of Quinazoline (VII-i)

Achiral HPLC

HPLC Column: Zorbax SB C-18, 25 cm, 50° C., 250 nm, flow 1.1. A: $H_2O$ (0.05% TFA) B: $CH_3CN$. 60% B to 90% in 5 min. to 95% in 6 min., stop time 9 min. Retention times: (IV-i), 3.9 min.; diastereomer of (IV-i), 3.8 min.; (VII-i), 6.4 min.; toluene, 4.5 min.; diastereomer of (VII-i), 6.5 min.; isomer of (VII-i), 6.2 min.

Achiral HPLC

HPLC Eclipse column XDB C-18, 25 cm×4.6 mm id; mobile phase acetonitrile—10 mM $NaH_2PO_4$ buffer, pH3.6, 40° C., flow 1.5 mL/min., 35% $CH_3CN$ to 95% in 15 min.; 245 nm, inj vol 5 uL, stop time 20 min., post time 3 min. Retention times: (IV-i), 8.8 min.; diastereomer of (VI-i), 8.5 min.; (VII-i), 13.3 min.; diastereomer of (VII-i), 13.5 min.

Alternative Preparation of Quinazoline (VII-i) from Quinazolinone (IV-i) (Scheme 5)

A first reactor (250 mL) is inerted and filled with $N_2$, then 200 mL of 2M BuMgCl/THF is charged to the reactor. CPA (36 mL, 420 mmoles) is added to the reactor with cooling to maintain a temperature of 35° C. Heat the solution for 1 h at 35° C.

A second low temperature reactor is inerted and filled with $N_2$, then the reactor is charged with solid (IV-i) (20 g, 54 mmmol), followed by toluene (140 mL) and N-methylmorpholine, NMM, (13.7 g, 135 mmol) at 20° C. The contents of reaction is cooled to −5 to 0° C., and thionyl chloride (4.2 mL, 57 mmol) is added at a rate to maintain reaction temperature between −5 to 0° C. Another 13.5 g of NMM is added to the reaction mixture. Stir for 0.5 h at −5 to 0° C. After 0.5 h an aliquot is quenched with MeOH to determine the level of (V-i) formation via the MeOH adduct of the (V-i) by HPLC A % (criterion>94%). The precipitated salt is removed by filtration under a $N_2$ atmosphere, and the salt cake is rinsed with toluene (60 mL). The filtrate, a clear orange solution, is then cooled to <−60° C.

Slowly add the content of the first reactor (62 mL, 122 mmol, 2.25 eq.) at a rate to maintain the lowest practical temperature during this exothermic reaction (<−50° C.). PCT: After 1.0 hour quench an aliquot with MeOH to determine the level of reaction completion of all products relative to MeOH adducts of compound (V-i) by HPLC A % (criterion: >97%). The reaction solution is then transferred to a vessel containing a solution of 12% aqueous citric acid (150 mL) at 20° C. The addition rate of the cold reaction to the quench mixture is controlled so as to keep the water from freezing. The mixture temperature is raised to 20° C., stirred for 0.5 h, and the layers are separated. Water (150 mL) is added to the organic layer, and the mixture is stirred for 0.5 h, and the layers are separated. The aqueous layer contain only traces of compound (VII-i), and is at pH 5–7. The organic layer is collected and put in a round bottom flask fitted with a distillation head. The content of the flask is concentrated by distillation to ~30% of its starting volume (thus removing CPA, THF, water and most of the toluene). During this distillation the product typically begins to crystallize. Methanol is then added to the round bottom flask, and then the solvent mixture of toluene and methanol is distilled until the toluene-methanol azeotrope has a composition of at most 5% toluene (or at least 95% toluene in the distillate). The final volume in the round bottom flask is approximately half of the starting volume. The slurry is cooled from 63° C. to 5° C. over ~6 h and aged for 1 h at 5° C. The solid is filtered and rinsed with cold methanol and dried in a vacuum oven at 40–50° C. to give a white solid compound (VII-i) in 80% yield. The product is 98+% pure and usually contains only traces of diastereomer, enantiomer, and pentenyne analogs.

Preparation of Quinazoline (I-i) from Quinazoline (VII-i) Ionization with Trifluoroacetic Acid A 100 gallon reactor was charged with ~22 kg of (VII-i) and the jacket temperature was set to 0° C. The vessel was then charged slowly with 65 kg of TFA. To the solution was added 2.2 L of USP water dropwise. The mixture was warmed to ambient temperature (20 to 25° C.) and held for 1 hour. After 1 hour, a sample of the mixture was analyzed for conversion to (I-i).

PCT: Criterion for complete conversion was >99 area % consumption of (VII-i) as indicated by HPLC analysis.

To the reaction mixture was added 95 kg of toluene, and the solution was cooled to 0° C. The vessel was then charged with 76.2 kg of 30 wt/vol. (10 M) aqueous NaOH while the temperature was maintained below 20° C. The mixture was stirred for 1 hour and a sample of the aqueous layer was withdrawn for a pH determination.

PCT-2: The criterion for the pH of aqueous phase was: pH 7 to 12.

The mixture was heated to 40 to 50° C., and the phases separated. Water (110 L USP) was charged and the resultant solution mixed for 30 minutes. The phases were permitted to separate at 40 to 50° C. for 30 minutes, and the aqueous phase was drained. The crude product solution was weighed, and sampled for solution yield analysis. The crude solution was charged to a distillation vessel through a 5.0 μm filter to remove any particulate matter and salts. The reaction mixture was concentrated (~2 to 3 L/kg of solvent relative to (I-i)) by distillation. The solution was cooled to ~90° C. and 75 kg of heptanes were added.

The mixture was cooled to ambient temperature and sampled to determine the precipitation profile. Specifically, the mother liquors were analyzed by HPLC for wt. % (I-i). Typical values were ~2.0 to 4.0 wt. % at ambient temperature. The mixture was cooled to 0 to 5° C. and sampled at 1 hour intervals until the precipitation profile was acceptable. When the final wt. % was <1.0 wt. %, the precipitation was determined to be complete.

The product was filtered and the mother liquors removed under vacuum for 15 minutes. The cake was washed with 40 kg of cold (0° C.) heptanes and dried on the filter for 30 minutes. The product was tranfered to trays and oven dried at 90° C. under 50 mm Hg vacuum until a constant weight was achieved. Final yield was about 80%; to provide 13.2 kg of compound (I-i).

Ionization with formic acid

A reactor was charged with 96% formic acid (250 mL), followed by (VII-i) (50 g, 19.39 mmol). The resulting slurry was heated to about 60 to 65° C., held for about 2 h, and the temperature decreased to roughly 40° C. PCT: <0.5 area % of (VII-i) by HPLC at 245 nm at about 1000 mAu. Toluene (250 mL) was charged to the reactor, followed by water (250 mL), and the resulting mixture warmed to 35 to 40° C. The mixture was stirred for about 0.5 hours, and held static for about 0.5 hours, and the phases separated.

Water (250 mL) was charged to the reactor, and the mixture was warmed to 35 to 40° C. The mixture was stirred for about 0.5 h and held static for about 0.5 hours. The phases were separated and the pH of the aqueous phase was found to be about 2.

A low pressure distillation was performed at 60 to 65° C., to an end volume of about 100 mL. The vacuum was broken and the vessel was slowly charged with methanol (375 mL) with the use of an addition funnel. Atmospheric distillation was carried out at between 63 to 64° C., to an end volume of about 100 mL. Methanol (200 mL) was charged, and the distillation was resumed to an end volume of about 100 mL. The mixture was held at about 60° C. to assure that the solids did not crash out of solution. A sample was submitted for G.C. solvent composition analysis. The solution met the criteria of <1.2 V % toluene by GC.

The temperature was held at 60° C. for about 2 hours, followed by cooling over a 2 hour period to about 0 to 5° C. The mixture was held at this temperature while a sample of the solution was analyzed for wt % (I-i). The solution contained <4.2 wt % (I-i), and the batch was filtered. The cake was washed with room temperature heptane (200 mL). The house vacuum was pulled on the cake for about 1 hour, after which the cake was distributed on a tray with about a 1 to 1.5 inch depth.

The tray was placed in the oven, a vacuum was established at room temperature and was held for about 2 hours. The temperature was then raised to 90° C., and held for about 2 hours. The temperature was then raised to about 120° C. for about 2 hours, after which a small sample was removed (0.2 to 0.5 g). The sample was lightly ground until uniform consistency with a mortar and pestle, and submitted for DSC and XRD analysis. The isolated solids had a weight of 31.8 g; which was equivalent to an 85% yield.

What is claimed is:

1. A process for the preparation of a compound of formula (I):

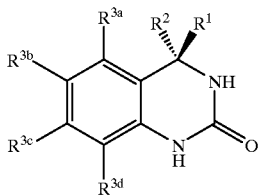

(I)

wherein:

$R^1$ is $C_{1-3}$ alkyl substituted with 1–7 halogen;

$R^2$ is selected from $C_{1-5}$ alkyl substituted with 1–2 $R^4$, $C_{2-5}$ alkenyl substituted with 1–2 $R^4$, $C_{2-5}$ alkynyl substituted with 1 $R^4$, and $OR^{2a}$;

$R^{2a}$ is $C_{1-4}$ alkyl;

$R^{3a}$ is H;

$R^{3b}$ is selected from H, $C_{1-4}$ alkyl, $C_{1-4}$ alkoxy, F, Cl, Br, I, and $NR^5R^{5a}$;

$R^{3c}$ is selected from H, $C_{1-4}$ alkyl, $C_{1-4}$ alkoxy, F, Cl, Br, I, and $NR^5R^{5a}$;

$R^{3d}$ is selected from H, $C_{1-4}$ alkyl, $C_{1-4}$ alkoxy, F, Cl, Br, I, and $NR^5R^{5a}$;

alternatively, $R^{3a}$ and $R^{3b}$ combine to form $-OCH_2O-$;

$R^4$ is selected from $C_{3-5}$ cycloalkyl substituted with 0–2 $R^{4a}$, phenyl substituted with 0–5 $R^{4a}$, and a 5–6 membered heterocyclic system containing 1–3 heteroatoms selected from O, N, and S, substituted with 0–2 $R^{4a}$;

$R^{4a}$ is selected from $C_{1-3}$ alkyl, Cl, Br, F, I, $OCH_3$, $SCH_3$, and $NR^5R^{5a}$; and $R^5$ and $R^{5a}$ are independently selected from H and $C_{1-3}$ alkyl;

the process comprising:

step (1), contacting a compound of formula (II):

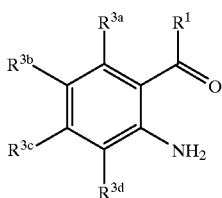

(II)

or a salt form or a hydrate of the salt form thereof;

with an isocyanate of formula (III):

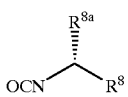

(III)

wherein:

$R^{8a}$ is selected from methyl, ethyl, propyl, and isopropyl;

$R^8$ is selected from phenyl substituted with 0–3 $R^9$, and naphthyl substituted with 0–3 $R^9$; and $R^9$ is selected from $C_{1-4}$ alkyl, $C_{1-4}$ alkoxy, F, Cl, Br, and I;

to form a compound of formula (II-a):

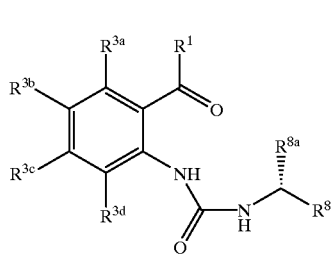

(II-a)

or a salt form thereof;

step (1-i), cyclizing the compound of formula (II-a) to form a compound of formula (IV):

(IV)

step (2), dehydrating the compound of formula (IV) to form a compound of formula (V):

(V)

step (2-i), contacting the compound of formula (V) with a nucleophile of formula (VI):

$R^2-M$    (VI)

wherein M is a metal counterion;

to form a compound of formula (VII):

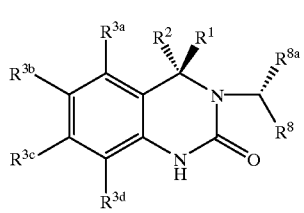

(VII)

or a salt form thereof; and step (3), ionizing the compound of formula (VII) to form a compound of formula (I), or a pharmaceutically acceptable salt form thereof.

2. The process according to claim 1, wherein:

$R^1$ is $CF_3$;

R² is selected from ethene substituted with cyclopropyl and ethyne substituted with cyclopropyl;
R³ᵃ is H;
R³ᵇ is Cl;
R³ᶜ and R³ᵈ are H;
R⁸ᵃ is CH₃;
R⁸ is phenyl;
M is a counter ion selected from Li⁺, Na⁺, K⁺, CuCl⁺, CuBr⁺, MgCl⁺, MgI⁺, and MgBr⁺; and wherein:
step (1) comprises contacting the compound of formula (II) with the isocyanate of formula (III) in the presence of a first strong acid;
step (1-i) comprises cyclizing the compound of formula (II-a) by heating the compound of formula (II-a) to a temperature in the range of about 50° C. to about 70° C.;
step (2) comprises dehydrating the compound of formula (IV) by contacting the compound of formula (IV) with at least one equivalent of a dehydrating agent in the presence of suitable amount of a base;
step (2-i) comprises contacting the compound of formula (V) with the nucleophile of formula (VI) by adding the nucleophile of formula (VI) to the compound of formula (V) at a suitable temperature to form the compound of formula (VII); and
step (3) comprises ionizing the compound of formula (VII) by contacting the compound of formula (VII) with a second strong acid to form a compound of formula (I) or a pharmaceutically acceptable salt form thereof.

3. The process according to claim 2, wherein:
the first strong acid is selected from trifluoroacetic acid, formic acid, methanesulfonic acid, nitric acid, sulfuric acid, hydrochloric acid; trimethylsilyl chloride, trimethylsilyl iodide, trimethylsilyl bromide, trimethyl silyl cyanide, triisopropylsilyl chloride, t-butyldimethylsilyl chloride, t-butyldiphenylsilyl chloride, triethylsilyl chloride, and trimethylsilyl trifluoromethanesulfonate;
the dehydrating agent is selected from methanesulfonyl chloride, thionyl chloride, acetyl chloride, and triphenylphosphine;
the amount of base in step (2) is in the range of about 2 to about 7 molar equivalents and the base is selected from triethylamine, N-methylmorpholine, N,N-diisopropylethylamine, pyridine, 1,4-diazabicyclo[2.2.2]octane, 1,8-diazabicyclo[5.4.0]undec-7-ene, tetramethylethylenediamine, and N,N-dimethylaminopyridine;
the suitable temperature to form the compound of formula (VII) is less than 0° C.; and
the second strong acid is selected from trifluoroacetic acid, formic acid, and methanesulfonic acid.

4. The process according to claim 3, wherein
the first strong acid is hydrochloric acid, the dehydrating agent is thionyl chloride, the base is triethylamine, and the second strong acid is formic acid.

5. The process according to claim 3, wherein the first strong acid is trimethylsilyl chloride.

6. The process according to claim 3, wherein the base is N-methylmorpholine.

7. The process according to claim 3: the first strong acid is trimethylsilyl chloride, the dehydrating agent is thionyl chloride, the base is N-methylmorpholine, and the second strong acid is formic acid.

8. A process for the preparation of a compound of formula (VII):

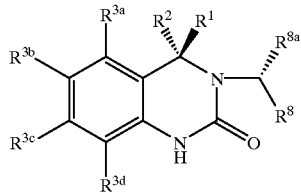

(VII)

or a salt form thereof; wherein:
R¹ is C₁₋₃ alkyl substituted with 1–7 halogen;
R² is selected from C₁₋₅ alkyl substituted with 1–2 R⁴, C₂₋₅ alkenyl substituted with 1–2 R⁴, C₂₋₅ alkynyl substituted with 1 R⁴, and OR²ᵃ;
R²ᵃ is selected from C₁₋₄ alkyl;
R³ᵃ is H;
R³ᵇ is selected from H, C₁₋₄ alkyl, C₁₋₄ alkoxy, F, Cl, Br, I, and NR⁵R⁵ᵃ;
R³ᶜ is selected from H, C₁₋₄ alkyl, C₁₋₄ alkoxy, F, Cl, Br, I, and NR⁵R⁵ᵃ;
R³ᵈ is selected from H, C₁₋₄ alkyl, C₁₋₄ alkoxy, F, Cl, Br, I, and NR⁵R⁵ᵃ;
alternatively, R³ᵃ and R³ᵇ combine to form —OCH₂O—;
R⁴ is selected from C₃₋₅ cycloalkyl substituted with 0–2 R⁴ᵃ, phenyl substituted with 0–5 R⁴ᵃ, and a 5–6 membered heterocyclic system containing 1–3 heteroatoms selected from O, N, and S, substituted with 0–2 R⁴ᵃ;
R⁴ᵃ is selected from C₁₋₃ alkyl, Cl, Br, F, I, OCH₃, SCH₃, and NR⁵R⁵ᵃ;
R⁵ and R⁵ᵃ are independently selected from H and C₁₋₃ alkyl;
R⁸ᵃ is selected from methyl, ethyl, propyl, and isopropyl;
R⁸ is selected from phenyl substituted with 0–3 R⁹, and naphthyl substituted with 0–3 R⁹; and
R⁹ is selected from C₁₋₄ alkyl, C₁₋₄ alkoxy, F, Cl, Br, and I;
the process comprising:
step (2), dehydrating a compound of formula (IV)

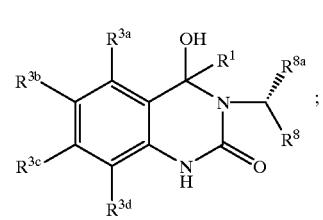

(IV)

to form a compound of formula (V):

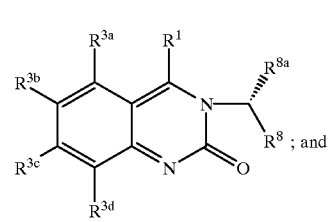

(V)

; and step (2-i), contacting the compound of formula (V) with a nucleophile of formula (VI):

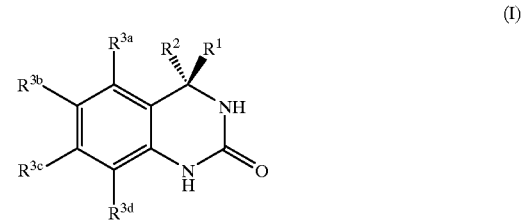

wherein M is a metal counterion;
to form a compound of formula (VII).

9. The process according to claim 8, wherein:
$R^1$ is $CF_3$;
$R^2$ is selected from ethene substituted with cyclopropyl and ethyne substituted with cyclopropyl;
$R^{3a}$ is H;
$R^{3b}$ is Cl;
$R^{3c}$ and $R^{3d}$ are H;
$R^{8a}$ is $CH_3$;
$R^8$ is phenyl; and
M is selected from $Li^+$, $Na^+$, $K^+$, $CuCl^+$, $CuBr^+$, $MgCl^+$, $MgI^+$ and $MgBr^+$.

10. The process according to claim 8, wherein the process is carried out in a suitable solvent, and further comprising crystallizing the compound of formula (VII) by contacting the suitable solvent with a crystallization solvent.

11. The process according to claim 8, wherein: step (2) comprises dehydrating the compound of formula (IV) by contacting the compound of formula (IV) with at least one equivalent of a dehydrating agent in the presence of a suitable amount of base to form a compound of formula (V); and
    step (2-i) comprises contacting the compound of formula (V) with the nucleophile of formula (VI) by adding the nucleophile of formula (VI) to the compound of formula (V) at a suitable temperature to form the compound of formula (VII).

12. The process according to claim 8, wherein: step (2) further comprises:
    a) contacting the compound of formula (IV) with at least one equivalent of a dehydrating agent in the presence of a base to form a compound of formula (V) and a precipitated amine salt of the base; and
    b) separating the precipitated amine salt of the base from the compound of formula (V).

13. The process according to claim 8, wherein: step (2) further comprises:
    a) contacting the compound of formula (IV) with at least one equivalent of a dehydrating agent in the presence of a base to form a compound of formula (V) and a precipitated amine salt of the base; and
    b) separating the precipitated amine salt of the base from the compound of formula (V) by filtration.

14. The process according to claim 11, wherein:
$R^1$ is $CF_3$;
$R^2$ is selected from ethene substituted with cyclopropyl and ethyne substituted with cyclopropyl;
$R^{3a}$ is H;
$R^{3b}$ is Cl;
$R^{3c}$ and $R^{3d}$ are H;
$R^{8a}$ is $CH_3$;
$R^8$ is phenyl; and
M is selected from $Li^+$ and $MgCl^+$.

15. The process according to claim 14, wherein:
the dehydrating agent is selected from methanesulfonyl chloride, thionyl chloride, acetyl chloride, and triphenylphosphine;
the amount of base is in the range of about 2 to about 7 molar equivalents and is selected from triethylamine, N-methylmorpholine, N,N-diisopropylethylamine, pyridine, 1,4-diazabicyclo[2.2.2]octane, 1,8-diazabicyclo[5.4.0]undec-7-ene, tetramethylethylenediamine, and N,N-dimethylaminopyridine; and
the suitable temperature to form the compound of formula (VII) is less than 0° C.

16. The process according to claim 8, further comprises:
step (3), ionizing the compound of formula (VII) to form a compound of formula (I):

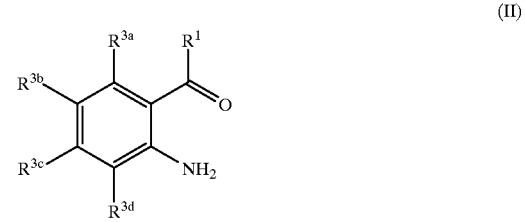

or a pharmaceutically acceptable salt form thereof.

17. The process according to claim 16, wherein step (3) comprises contacting the compound of formula (VII) with a strong acid selected from trifluoroacetic acid, formic acid, and methanesulfonic acid to form a compound of formula (I) or a pharmaceutically acceptable salt form thereof.

18. The process according to claim 8, wherein the compound of formula (IV) is prepared by the process comprising:
step (1), contacting a compound of formula (II):

or a salt form or a hydrate of the salt form thereof;
with an isocyanate of formula (III):

(III)

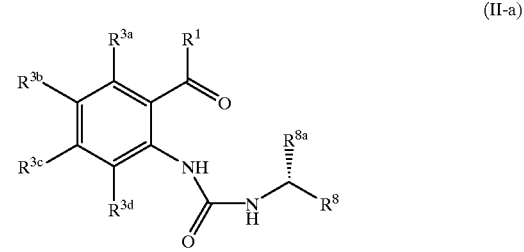

to form a compound of formula (II-a):

(II-a)

or a salt form thereof; and
step (1-i), cyclizing the compound of formula (II-a) to form a compound of formula (IV).

19. The process according to claim 18, wherein:

$R^1$ is $CF_3$;
$R^2$ is selected from ethene substituted with cyclopropyl, and ethyne substituted with cyclopropyl;
$R^{3a}$ is H;
$R^{3b}$ is Cl;
$R^{3c}$ and $R^{3d}$ are H;
$R^{8a}$ is $CH_3$;
$R^8$ is phenyl;
M is $MgCl^+$ or $Li^+$; and
the compound of formula (II) is the hydrate of the hydrochloride salt.

20. The process according to claim 19, wherein step (1-i) comprises cyclizing the compound of formula (II-a) by heating the compound of formula (II-a) to a temperature in the range of about 50° C. to about 70° C.

21. The process according to claim 18, wherein step (1) comprises contacting the compound of formula(II) with the isocyanate of formula (III) in the presence of an acid selected from hydroiodic acid, hydrobromic acid, hydrochloric acid, sulfuric acid, nitric acid, acetic acid, toluenesulfonic acid, benzene sulfonic acid, trimethylsilyl chloride, trimethylsilyl iodide, trimethylsilyl bromide, trimethyl silyl cyanide, triisopropylsilyl chloride, t-butyldimethylsilyl chloride, t-butyldiphenylsilyl chloride, triethylsilyl chloride, and trimethylsilyl trifluoromethanesulfonate.

22. A process for the preparation of a compound of formula (I):

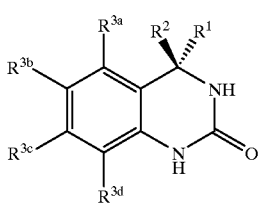

(I)

wherein:
$R^1$ is selected from $C_{1-3}$ alkyl substituted with 1–7 halogen, and $C_{2-5}$ alkynyl substituted with 1 $R^4$;
$R^2$ is selected from $CF_3$, $C_{1-5}$ alkyl substituted with 1–2 $R^4$, $C_{2-5}$ alkenyl substituted with 1–2 $R^4$, $C_{2-5}$ alkynyl substituted with 1 $R^4$, and $OR^{2a}$;
$R^{2a}$ is selected from $C_{1-4}$ alkyl;
$R^{3a}$ is H;
$R^{3b}$ is selected from H, $C_{1-4}$ alkyl, $C_{1-4}$ alkoxy, F, Cl, Br, I, and $NR^5R^{5a}$;
$R^{3c}$ is selected from H, $C_{1-4}$ alkyl, $C_{1-4}$ alkoxy, F, Cl, Br, I, and $NR^5R^{5a}$;
$R^{3d}$ is selected from H, $C_{1-4}$ alkyl, $C_{1-4}$ alkoxy, F, Cl, Br, I, and $NR^5R^{5a}$;
alternatively, $R^{3a}$ and $R^{3b}$ combine to form —$OCH_2O$—;
$R^4$ is selected from $C_{3-5}$ cycloalkyl substituted with 0–2 $R^{4a}$, phenyl substituted with 0–5 $R^{4a}$, and a 5–6 membered heterocyclic system containing 1–3 heteroatoms selected from O, N, and S, substituted with 0–2 $R^{4a}$;
$R^{4a}$ is selected from $C_{1-3}$ alkyl, Cl, Br, F, I, $OCH_3$, $SCH_3$, and $NR^5R^{5a}$; and
$R^5$ and $R^{5a}$ are independently selected from H and $C_{1-3}$ alkyl;

the process comprising:
step (1), contacting a compound of formula (II):

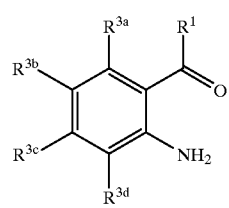

(II)

or a salt form or a hydrate of the salt form thereof;
with an isocyanate of formula (III):

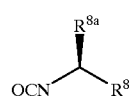

(III)

wherein:
$R^{8a}$ is selected from methyl, ethyl, propyl, and isopropyl;
$R^8$ is selected from phenyl substituted with 0–3 $R^9$, and naphthyl substituted with 0–3 $R^9$; and
$R^9$ is selected from $C_{1-4}$ alkyl, $C_{1-4}$ alkoxy, F, Cl, Br, and I;
to form a compound of formula (II-a):

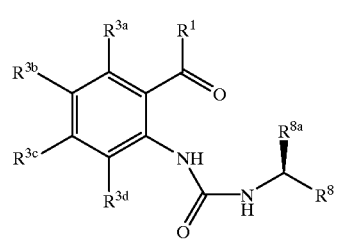

(II-a)

or a salt form thereof;
step (1-i), cyclizing the compound of formula (II-a) to form a compound of formula (IV):

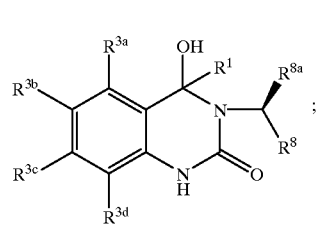

(IV)

step (2), dehydrating the compound of formula (IV): to form a compound of formula (V):

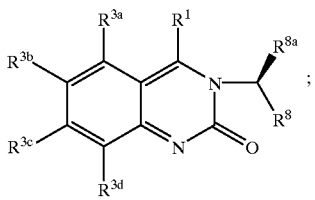

(V)

(2-i) contacting the compound of formula (V) with a nucleophile of formula (VI):

$R^2$—M  (VI)

wherein M is a metal counterion;
to form a compound of formula (VII):

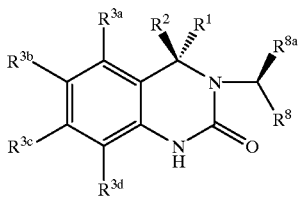

(VII)

or a salt form thereof; and
step (3), ionizing the compound of formula (VII) to form a compound of formula (I), or a pharmaceutically acceptable salt form thereof.

23. A compound of formula (IV):

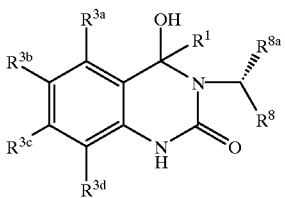

(IV)

wherein:
$R^1$ is $C_{1-3}$ alkyl substituted with 1–7 halogen;
$R^2$ is selected from $C_{1-5}$ alkyl substituted with 1–2 $R^4$, $C_{2-5}$ alkenyl substituted with 1–2 $R^4$, $C_{2-5}$ alkynyl substituted with 1 $R^4$, and $OR^{2a}$;
$R^{2a}$ is selected from $C_{1-4}$ alkyl;
$R^{3a}$ is H;
$R^{3b}$ is selected from H, $C_{1-4}$ alkyl, $C_{1-4}$ alkoxy, F, Cl, Br, I, and $NR^5R^{5a}$;
$R^{3c}$ is selected from H, $C_{1-4}$ alkyl, $C_{1-4}$ alkoxy, F, Cl, Br, I, and $NR^5R^{5a}$;
$R^{3d}$ is selected from H, $C_{1-4}$ alkyl, $C_{1-4}$ alkoxy, F, Cl, Br, I, and $NR^5R^{5a}$;
alternatively, $R^{3a}$ and $R^{3b}$ combine to form —OCH$_2$O—;
$R^4$ is selected from $C_{3-5}$ cycloalkyl substituted with 0–2 $R^{4a}$, phenyl substituted with 0–5 $R^{4a}$, and a 5–6 membered heterocyclic system containing 1–3 heteroatoms selected from O, N, and S, substituted with 0–2 $R^{4a}$;
$R^{4a}$ is selected from $C_{1-3}$ alkyl, Cl, Br, F, I, OCH$_3$, SCH$_3$, and $NR^5R^{5a}$;

$R^5$ and $R^{5a}$ are independently selected from H and $C_{1-3}$ alkyl;
$R^{8a}$ is selected from methyl, ethyl, propyl, and isopropyl;
$R^8$ is selected from phenyl substituted with 0–3 $R^9$, and naphthyl substituted with 0–3 $R^9$; and
$R^9$ is selected from $C_{1-4}$ alkyl, $C_{1-4}$ alkoxy, F, Cl, Br, and I.

24. The compound of formula (VII):

(VII)

or a salt form thereof; wherein:
$R^1$ is $C_{1-3}$ alkyl substituted with 1–7 halogen;
$R^2$ is selected from $C_{1-5}$ alkyl substituted with 1–2 $R^4$, $C_{2-5}$ alkenyl substituted with 1–2 $R^4$, $C_{2-5}$ alkynyl substituted with 1 $R^4$, and $OR^{2a}$;
$R^{2a}$ is selected from $C_{1-4}$ alkyl;
$R^{3a}$ is H;
$R^{3b}$ is selected from H, $C_{1-4}$ alkyl, $C_{1-4}$ alkoxy, F, Cl, Br, I, and $NR^5R^{5a}$;
$R^{3c}$ is selected from H, $C_{1-4}$ alkyl, $C_{1-4}$ alkoxy, F, Cl, Br, I, and $NR^5R^{5a}$;
$R^{3d}$ is selected from H, $C_{1-4}$ alkyl, $C_{1-4}$ alkoxy, F, Cl, Br, I, and $NR^5R^{5a}$;
alternatively, $R^{3a}$ and $R^{3b}$ combine to form —OCH$_2$O—;
$R^4$ is selected from $C_{3-5}$ cycloalkyl substituted with 0–2 $R^{4a}$, phenyl substituted with 0–5 $R^{4a}$, and a 5–6 membered heterocyclic system containing 1–3 heteroatoms selected from O, N, and S, substituted with 0–2 $R^{4a}$;
$R^{4a}$ is selected from $C_{1-3}$ alkyl, Cl, Br, F, I, OCH$_3$, SCH$_3$, and $NR^5R^{5a}$;
$R^5$ and $R^{5a}$ are independently selected from H and $C_{1-3}$ alkyl;
$R^{8a}$ is selected from methyl, ethyl, propyl, and isopropyl;
$R^8$ is selected from phenyl substituted with 0–3 $R^9$, and naphthyl substituted with 0–3 $R^9$; and
$R^9$ is selected from $C_{1-4}$ alkyl, $C_{1-4}$ alkoxy, F, Cl, Br, and I.

25. The compound according to claim 24, wherein the compound of formula (VII) is (VII-i):

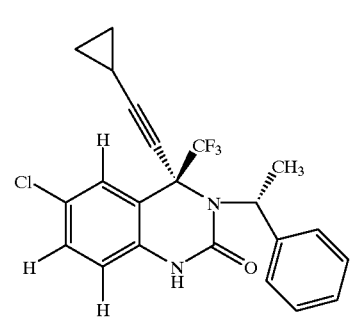

(VII-i)

or a salt form thereof.

* * * * *